US012680068B2

(12) United States Patent
Chen et al.

(10) Patent No.: US 12,680,068 B2
(45) Date of Patent: Jul. 14, 2026

(54) BIOLOGICAL REACTION APPARATUS AND METHOD FOR PERFORMING BIOLOGICAL DETECTION ON BASIS OF APPARATUS

(71) Applicant: NANJING GENSCRIPT BIOTECH CO., LTD., Nanjing (CN)

(72) Inventors: Xin Chen, Nanjing (CN); Chao Wang, Nanjing (CN); Jian Yu, Nanjing (CN)

(73) Assignee: NANJING GENSCRIPT BIOTECH CO., LTD., Nanjing (CN)

( * ) Notice: Subject to any disclaimer, the term of this patent is extended or adjusted under 35 U.S.C. 154(b) by 1249 days.

(21) Appl. No.: 17/594,999

(22) PCT Filed: May 22, 2020

(86) PCT No.: PCT/CN2020/091676

§ 371 (c)(1),
(2) Date: Nov. 4, 2021

(87) PCT Pub. No.: WO2020/238769

PCT Pub. Date: Dec. 3, 2020

(65) Prior Publication Data

US 2022/0204913 A1    Jun. 30, 2022

(30) Foreign Application Priority Data

May 24, 2019    (CN) ......................... 201910439559.7

(51) Int. Cl.
*C12M 1/34*        (2006.01)
*C12M 1/36*        (2006.01)
*G01N 35/00*       (2006.01)

(52) U.S. Cl.
CPC ............ *C12M 41/36* (2013.01); *C12M 41/48* (2013.01); *G01N 35/00584* (2013.01)

(58) Field of Classification Search
CPC ...................................................... C12M 41/36
See application file for complete search history.

(56) References Cited

U.S. PATENT DOCUMENTS 3,892,197 A      7/1975   Kinney et al.
5,459,069 A  *  10/1995   Palsson ................ C07K 14/535
                                                   435/293.1

(Continued)

FOREIGN PATENT DOCUMENTS

CN        107588997 A      1/2018
CN        107907396 A  *   4/2018    ............... G01N 1/31

(Continued)

OTHER PUBLICATIONS

The Extended European Search Report in European Application No. 20812547.6 mailed on May 24, 2022, 9 pages.

(Continued)

*Primary Examiner* — Michael A Marcheschi
*Assistant Examiner* — Jonathan E Lepage
(74) *Attorney, Agent, or Firm* — Metis IP LLC

(57) ABSTRACT

A biological reaction apparatus used for biological macro-molecules includes a power supply module (1), a control module (2), a liquid processing module (3), a reactor module (4) and a sensor (5); the power supply module (1) includes a direct current power supply (6) and a switch (7); the control module (2) includes a system controller (8), an input device (9) and an output device (10); the liquid processing module (3) includes a valve (11) or a combination of valves (11), a pump (12) or a combination of pumps (12) and sample cells (13); the reactor module (4) includes a reactor (14); the reactor (14) includes a reactor frame (15) and a reactor cavity (16) formed by the reactor frame (15). The apparatus has a simple and practical structure and is easy to operate. In the reactor (14), a very small amount of a reagent is used to achieve a uniform and highly-sensitive reaction.

15 Claims, 42 Drawing Sheets

(56) References Cited

U.S. PATENT DOCUMENTS

| 2004/0213083 A1 * | 10/2004 | Fujiwara ................. B01F 33/81 |
| | | 366/336 |
| 2005/0014134 A1 | 1/2005 | West et al. |
| 2008/0153080 A1 * | 6/2008 | Mantecon .............. C12M 21/02 |
| | | 435/162 |
| 2014/0050622 A1 | 2/2014 | Kitagawa et al. |
| 2016/0132402 A1 * | 5/2016 | Shin ................. G01N 35/00069 |
| | | 714/19 |
| 2017/0205222 A1 * | 7/2017 | Mathuis ................. G01N 15/14 |

FOREIGN PATENT DOCUMENTS

| CN | 108548695 A | 9/2018 |
| CN | 108593952 A | 9/2018 |
| CN | 109238811 A | 1/2019 |
| CN | 210269875 U | 4/2020 |
| EP | 1605243 A1 | 12/2005 |
| EP | 2927663 A1 | 10/2015 |
| EP | 3252452 A1 | 12/2017 |
| GB | 2544769 A * | 5/2017 | ........ B01L 3/502784 |
| JP | 10267801 A * | 10/1998 |
| JP | 2015004552 A | 1/2015 |
| KR | 20120094873 A | 8/2012 |
| WO | WO-2006107684 A2 * | 10/2006 | .......... G01N 1/4005 |
| WO | 2014075693 A1 | 5/2014 |
| WO | 2017132637 A2 | 8/2017 |
| WO | 2018182757 A1 | 10/2018 |

OTHER PUBLICATIONS

International Search Report in PCT/CN2020/091676 mailed on Aug. 27, 2020, 8 pages.
Written Opinion in PCT/CN2020/091676 mailed on Aug. 27, 2020, 8 pages.

* cited by examiner

114

125

116

115

117

BSA

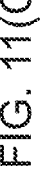
FIG. 11(D)
FIG. 11(C)

1  2  3  4  5  6  7  8

1  2  3  4  5  6  7  8

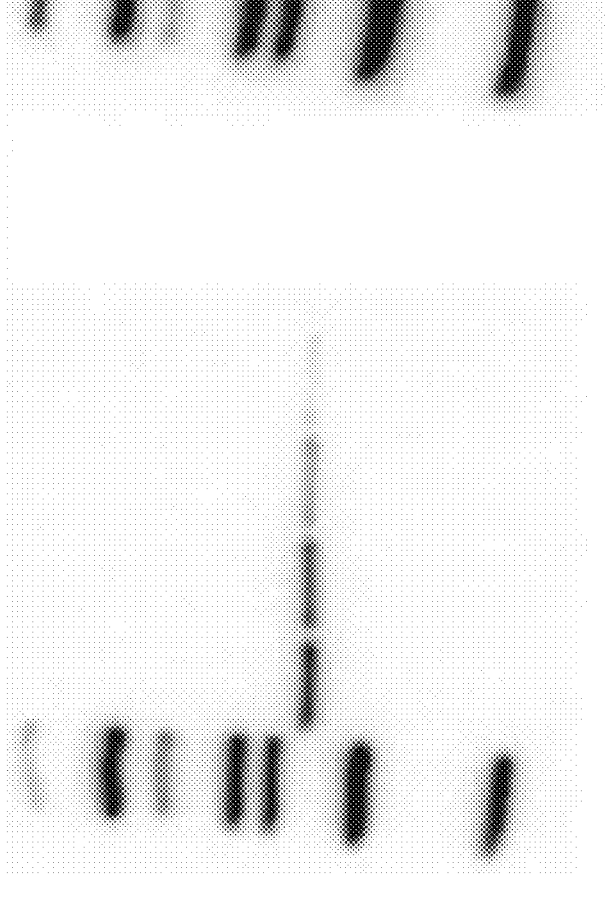
FIG. 13(B)
FIG. 13(A)

BIOLOGICAL REACTION APPARATUS AND METHOD FOR PERFORMING BIOLOGICAL DETECTION ON BASIS OF APPARATUS

CROSS-REFERENCE TO RELATED APPLICATIONS

This application is a U.S. national stage under 35 U.S.C. § 371 of International Application No. PCT/CN2020/091676, filed on May 22, 2020 designating the United States of America, which claims the priority of Chinese Patent Application No. 201910439559.7 filed on May 24, 2019, the entire contents of which are hereby incorporated by reference.

TECHNICAL FIELD

The present disclosure relates to the technical field of biology, in particular to a biological reaction apparatus and a method for performing biological detection on basis of the apparatus.

BACKGROUND

Common detection methods for biological macromolecules include forming feedback signals on basis of structures of biological macromolecules and detection reagents.

Common experimental methods are as follows:
1. Protein Detection
   A) Gel or other vectors with proteins are put into a staining solution;
   B) stains are bound to the proteins by vibration and heating;
   C) the stained gel and the like are put into a destaining solution; and
   D) stains not bound to the proteins are removed from the gel and the like by vibration and heating.
2. Nucleic Acid Detection
   A) Gel or other vectors with nucleic acid are put into a staining solution;
   B) stains are bound to the nucleic acid by vibration and heating;
   C) the stained gel and the like are put into a destaining solution; and
   D) stains not bound to the nucleic acid are removed from the gel and the like by vibration and heating.
3. Probe Detection
   A) Vectors with samples are put into a blocking solution;
   B) an unbound sample area is rapidly bound to a blocking substance by vibration and heating;
   C) the blocked vectors are put into a probe solution;
   D) probes are rapidly bound to the samples by vibration and heating;
   E) the vectors are put into a cleaning solution; and
   F) non-specifically bound probes are washed away by vibration and heating.

A general detection method for biological macromolecules can be described as a soaking method. Soaking is performed in a large amount of a solution, and specific binding and non-specific removal are performed by thermal motion of molecules. Although the thermal motion of molecules can be accelerated by vibration, heating, ultrasound, microwave and other ways, existing defects, such as high consumption of time and labors, waste of reagents, low repeatability and low uniformity, are still unavoidable.

Therefore, it is of great practical significance to provide an automatic biological reaction apparatus for detecting biological macromolecules.

SUMMARY

In view of this situation, the present disclosure provides a biological reaction apparatus and a method for performing biological detection on basis of the apparatus. The apparatus has a simple and practical structure and is easy to operate. In a reactor, a very small amount of a reagent is used to achieve a uniform and highly-sensitive reaction.

To achieve the foregoing inventive objectives, the present disclosure provides the following technical solutions:

The present disclosure provides a biological reaction apparatus, including a power supply module 1, a control module 2, a liquid processing module 3, a reactor module 4 and a sensor 5; the power supply module 1 includes a direct current power supply 6 and a switch 7; the control module 2 includes a system controller 8, an input device 9 and an output device 10; the liquid processing module 3 includes a valve 11 or a combination of valves 11, a pump 12 or a combination of pumps 12 and sample cells 13; the reactor module 4 includes a reactor 14; and the reactor 14 includes a reactor frame 15 and a reactor cavity 16 formed by the reactor frame 15; the power supply module 1 is separately connected to the control module 2, the liquid processing module 3 and the reactor module 4 through cables 25; the control module 2 is separately connected to the liquid processing module 3 and the reactor module 4 through the cables 25; the liquid processing module 3 is connected to the reactor module 4 through a pipeline 26; and the control module 2 is connected to the reactor module 4 through the sensor 5.

In some specific embodiments of the present disclosure, the reactor frame 15 is provided with at least one opening 17; and the opening 17 is connected to the pump 12 or the combination of pumps 12.

In some specific embodiments of the present disclosure, the reactor frame 15 is further provided with a pressing part 18.

In some specific embodiments of the present disclosure, the reactor frame 15 is further provided with a sealing part 19.

In some specific embodiments of the present disclosure, the reactor frame 15 includes a reactor front plate 20 and a reactor rear plate 21, and a limiting part 22 is also arranged between the reactor front plate 20 and the reactor rear plate 21. The limiting part is used to prevent the situation that since the stroke of 96 and 15 is too large during pressing, the volume of 16 is too small.

In some specific embodiments of the present disclosure, a mother liquid pool 23 is also arranged between the liquid processing module 3 and the reactor module 4.

In some specific embodiments of the present disclosure, at least one diversion block 24 is also arranged in the reactor cavity 16.

On basis of the researches above, the present disclosure also provides an application of the biological reaction apparatus in detection of biological samples.

The present disclosure also provides a biological sample detection method, including on basis of the biological reaction apparatus provided in the present disclosure, putting a vector carrying a reactant into the reactor cavity 16, putting a reaction liquid into the sample cells 13 of the liquid processing module 3 and turning on the control module 2 by the power supply module 1 to control the pump 12 or the combination of pumps 12 of the liquid processing module 3 to deliver the reaction liquid in the sample cells (13) into the reactor cavity 16, so as to make the reaction liquid mixed with the vector carrying the reactant for reaction and detection.

According to the automatic biological reaction apparatus provided in the present disclosure, the whole process can be completed automatically by only placing a sample and a reaction solution to specific positions and setting a program.

It is shown through experiments that:

In a Coomassie brilliant blue staining test, on IgG, all bands in a traditional method and the present disclosure are visible, but the color in the present disclosure is darker. On BSA, the $10^{th}$ sample in the traditional method is visible, and all 12 samples in the present disclosure are visible, so that the sensitivity of the present disclosure is better. On lysozyme, the $9^{th}$ sample in the traditional method is visible, and the $11^{th}$ sample in the present disclosure is visible, so that the sensitivity of the present disclosure is better. It can be seen from FIG. 9(C), FIG. 9(D), FIG. 9(E) and Tables 2-4 that compared with the traditional method, the present disclosure has the advantages that the staining degree is increased by 4.49%-22.90% based on IgG detection results; the staining degree is increased by 14.87%-60.00% based on BSA detection results; and the staining degree is increased by 9.72%-28.37% based on lysozyme detection results. Compared with the traditional method, only 50% of reagents need to be used in the present disclosure, and the sensitivity and the staining degree of the present disclosure are better than those of the traditional method.

In a silver staining test, when half of the reagents are used, the sensitivity of the present disclosure is better than that of the traditional method, and the background is better than that of the traditional method. On IgG, all bands in the traditional method and the present disclosure are visible. On BSA, the $10^{th}$ sample in the traditional method is visible, and all 12 samples in the present disclosure are visible, so that the sensitivity of the present disclosure is better. It can be seen from FIG. 10(C), FIG. 10(D) and Tables 6-7 that compared with the traditional method, the method provided in the present disclosure has the advantages that the staining degree is increased by 114.91%-139.27% based on IgG detection results; and the staining degree is increased by 100.88%-186.47% based on BSA detection results. Compared with the traditional method, only 50% of reagents need to be used in the present disclosure, and the sensitivity and the staining degree are better than those of the traditional method.

In a WB1 test, on 93 kd, the $4^{th}$ lane in the traditional method is visible, and the $5^{th}$ lane in the present disclosure is visible, so that the sensitivity of the present disclosure is better. On 7 kd, the $8^{th}$ lane in the traditional method is visible, and the 9th lane in the present disclosure is visible, so that the sensitivity of the present disclosure is better. It can be seen from FIG. 11(E), FIG. 11(F) and Tables 9-10 that compared with the traditional method, the method provided in the present disclosure has the advantages that the staining degree is increased by 102.09%-507.93% based on 93 kd detection results; and the staining degree is increased by 20.61%-432.91% based on 7 kd detection results. Compared with the traditional method, only 74% of reagents and 80% of antibodies need to be used in the present disclosure, and the sensitivity and the signal intensity of the present disclosure are better than those of the traditional method.

In a WB2 test, the $6^{th}$ lane in the traditional method is visible, and the $8^{th}$ lane in the present disclosure is visible, so that the sensitivity of the present disclosure is better. It can be seen from FIG. 12(C) and Table 12 that compared with the traditional method, the method provided in the present disclosure has the advantages that the staining degree is increased by 3.05%-305.33% based on β-actin detection results. Compared with the traditional method, only 65% of reagents, 40% of antibodies and a shorter processing time need to be used in the present disclosure, and the sensitivity and the signal intensity of the present disclosure are better than those of the traditional method.

In a WB5 test, the color of FIG. 13(B) and FIG. 13(D) is darker than that of FIG. 13(A) and FIG. 13(C), and it can be seen from FIG. 13(E) and Table 13 that compared with the traditional method, the method provided in the present disclosure has the advantages that the staining degree is increased by 50.38%-108.84% based on GAPDH detection results. That is to say, the signal intensity is higher, and it is further shown that the effect of the present disclosure is better than that of the traditional method. Compared with the traditional method, only 66% of reagents need to be used in the present disclosure, and the sensitivity and the signal intensity of the present disclosure are better than those of the traditional method.

In a WB3 test, it can be seen from FIG. 14 that the $4^{th}$ lane in the traditional method is visible, and the $5^{th}$ lane in the present disclosure is visible, so that the sensitivity of the present disclosure is better. It can be seen from FIG. 14(C) and Table 15 that compared with the traditional method, the method provided in the present disclosure has the advantages that the staining degree is increased by 27.52%-603.57% based on β-actin detection results. Compared with the traditional method, only 30% of reagents and a shorter processing time need to be used in the present disclosure, and the sensitivity and the signal intensity of the present disclosure are better than those of the traditional method.

In a WB4 test, it can be seen from FIG. 15(D) and Table 16 that bands in the present disclosure are darker than those in the traditional method, and the staining degree is increased by 59.26%-111.13%, showing that the effect of the present disclosure is better. Compared with the traditional method, only 20% of reagents and a shorter processing time need to be used in the present disclosure, and the signal intensity of the present disclosure is better than that of the traditional method.

In summary, compared with the traditional method, the automatic biological reaction apparatus has the following advantages:

1. Time is saved. The system is fully automatic, a lot of labors are reduced, and the efficiency is greatly improved.
2. The sensitivity is high. Compared with the traditional method, the reaction efficiency is improved by liquid flow control, and thus the sensitivity is higher under conditions same as those in the traditional method.
3. Reactor reagents are reduced. In the automatic biological reaction apparatus, only a small amount of a liquid needs to be used in the reactor to complete a reaction requiring a large amount of reagents in the traditional method.

BRIEF DESCRIPTION OF THE DRAWINGS

To describe technical solutions in embodiments of the present disclosure or in the related art more clearly, the following briefly describes accompanying drawings required for describing the embodiments or the related art.

FIG. 5(A) is a schematic structural diagram of a biological reaction apparatus disclosed in Example 4 of the present disclosure; FIG. 5(B) to FIG. 5(D) are schematic structural diagrams of a biological reaction apparatus disclosed in Example 5 of the present disclosure; FIG. 5(B) is a front view; FIG. 5(C) is a cross-sectional view; FIG. 5(D) is a rear view; FIG. 5(E) to FIG. 5(G) are schematic structural diagrams of a biological reaction apparatus disclosed in Example 6 of the present disclosure; FIG. 5(E) is a front view; FIG. 5(F) is a cross-sectional view; and FIG. 5(G) is a rear view;

FIG. 6(A) is a front view; and FIG. 6(B) and FIG. 6(C) are side views, showing that a reactant is suspended in a liquid;

FIG. 8(A) is a schematic diagram of the two-way fast card; FIG. 8(B) is a schematic diagram of a fast card B113; FIG. 8(C) is a cross-sectional view of the fast card B113; FIG. 8(D) is a schematic diagram of a fast card A112; and FIG. 8(E) is a cross-sectional view of the fast card A112;

FIG. 9(A) shows staining results of a traditional method; FIG. 9(B) shows staining results of the present disclosure; FIG. 9(C) shows comparative analysis of the staining degree of IgG in the staining results of the traditional method and the staining results of the present disclosure; FIG. 9(D) shows comparative analysis of the staining degree of lysozyme in the staining results of the traditional method and the staining results of the present disclosure; and FIG. 9(E) shows comparative analysis of the staining degree of BSA in the staining results of the traditional method and the staining results of the present disclosure;

FIG. 10(A) shows staining results of the present disclosure; FIG. 10(B) shows staining results of a traditional method; FIG. 10(C) shows comparative analysis of the staining degree of IgG in the staining results of the traditional method and the staining results of the present disclosure; and FIG. 10(D) shows comparative analysis of the staining degree of BSA in the staining results of the traditional method and the staining results of the present disclosure;

FIGS. 11(A)-11(F) show results of Example 12; FIG. 11(A) to FIG. 11(B) show results of a traditional method; FIG. 11(C) to FIG. 11(D) show results of the method provided in the present disclosure; FIG. 11(E) shows comparative analysis of the staining degree of a 93 kd protein in the results of the traditional method and the results of the present disclosure; and FIG. 11(F) shows comparative analysis of the staining degree of a 7 kd protein in the results of the traditional method and the result of the present disclosure;

FIG. 12(A) shows results of a traditional method; FIG. 12(B) shows results of the present disclosure; and FIG. 12(C) shows comparative analysis of the staining degree of a β-actin protein in the results of the traditional method and the results of the present disclosure;

FIGS. 13(A)-13(E) show results of Example 16; FIG. 13(A) shows results of a film A; FIG. 13(B) shows results of a film B; FIG. 13(C) shows results of a film C; FIG. 13(D) shows results of a film D; and FIG. 13(E) shows comparative analysis of the staining degree of a GAPDH protein in the results of the traditional method and the results of the present disclosure;

FIG. 14(A) shows results of a traditional method; FIG. 14(B) shows results of the present disclosure; and FIG. 14(C) shows comparative analysis of the staining degree of a β-actin protein in the results of the traditional method and the results of the present disclosure;

FIGS. 15(A)-15(D) show results of Example 15; FIG. 15(A) shows results of a traditional method; FIG. 15(B) shows results of the present disclosure; FIG. 15(C) shows the liquid flow direction of a primary antibody mother liquid and a secondary antibody mother liquid added into corresponding reservoirs; and FIG. 15(D) shows comparative analysis of the staining degree of a 7 kd protein in the results of the traditional method and the results of the present disclosure;

Figure 1:
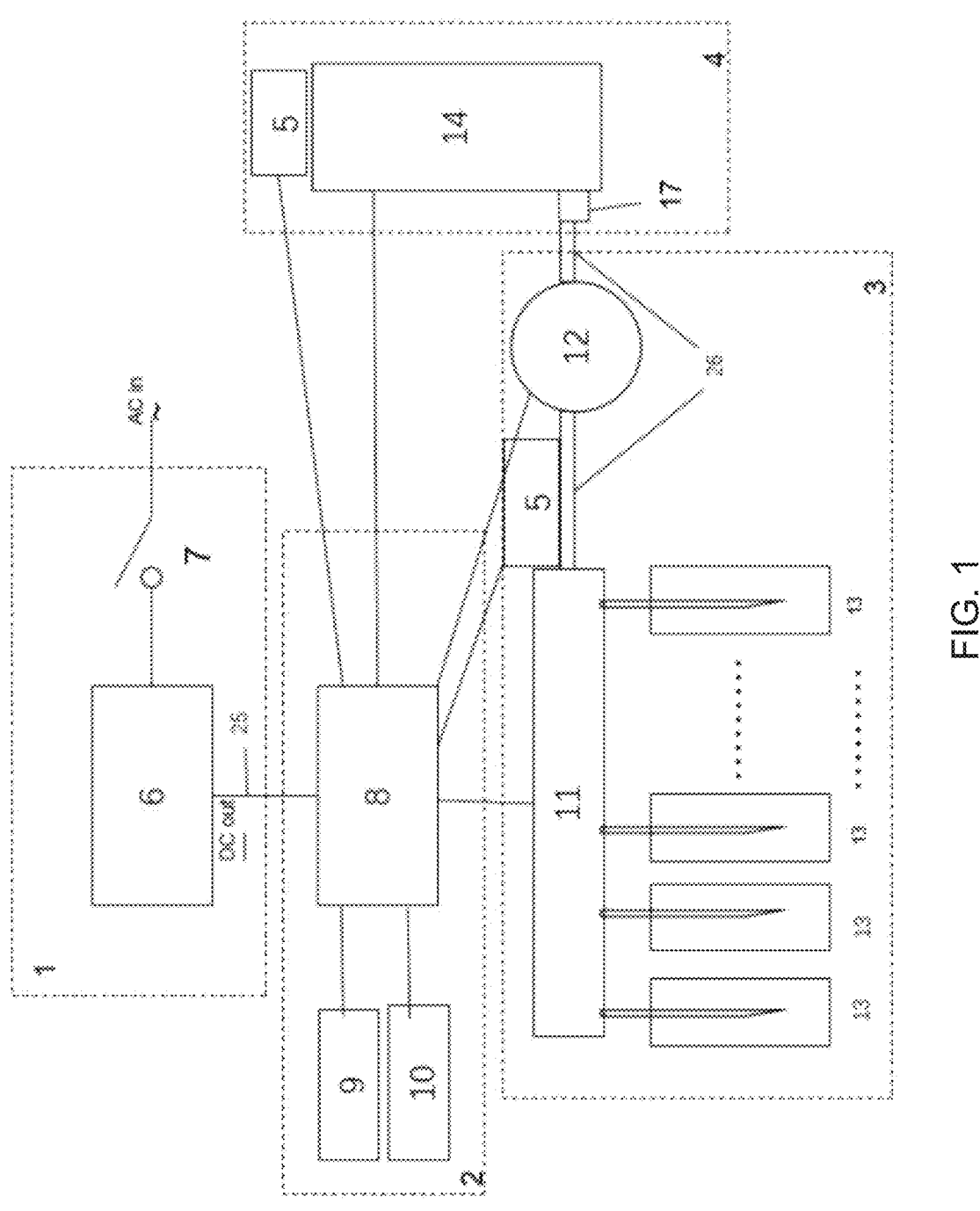
FIG. 1 is a schematic structural diagram of a biological reaction apparatus provided in Example 1 of the present disclosure.

Where, 1 refers to a power supply module; 2 refers to a control module; 3 refers to a liquid processing module; 4 refers to a reactor module; 5 refers to a sensor; 6 refers to a direct current power supply; 7 refers to a switch; 8 refers to a system controller; 9 refers to an input device; 10 refers to an output device; 11 refers to a valve; 12 refers to a pump; 13 refers to a sample cell; 14 refers to a reactor; 15 refers to a reactor frame; 16 refers to a reactor cavity; 17 refers to an opening; 18 refers to a pressing part; 19 refers to a sealing part; 20 refers to a reactor front plate; 21 refers to a reactor rear plate; 22 refers to a limiting part; 23 refers to a mother liquid pool; 24 refers to a diversion block; 25 refers to a cable; 26 refers to a pipeline;

17-1 refers to a liquid inlet; 17-2 refers to a liquid outlet; 27 refers to a waste liquid collector; 28 refers to a liquid level indicator; 29 refers to a reaction liquid inlet and outlet pipeline; 30 refers to a waste liquid discharge or air inlet pipeline; 50, 51, 52, 53, 54 and 55 each refers to a two-position three-way valve; 32, 33 and 34 refer to three liquid receiving ports of a two-position three-way valve, 33 is a common end, and 32 and 33 are in normally open connection; 38, 39 and 40 refer to three liquid receiving ports of a two-position three-way valve, 39 is a common end, and 38 and 39 are in normally open connection; 35, 36 and 37 refer to three liquid receiving ports of a two-position three-way valve, 36 is a common end, and 35 and 36 are in normally open connection; 41, 42 and 43 refer to three liquid receiving ports of a two-position three-way valve, 43 is a common end, and 42 and 43 are in normally open connection; 44, 45 and 46 refer to three liquid receiving ports of a two-position three-way valve, 44 is a common end, and 46 and 44 are in normally open connection; and 47, 48, 49 refer to three liquid receiving ports of a two-position three-way valve, 49 is a common end, and 47 and 49 are in normally open connection;

62 refers to a gas buffer bottle; 66, 67, 68, 69, 70, 71, 72 and 73 each refers to a selection connector of an eight-position valve; 74 refers to a common connector; 65 refers to a selection path, which is used to make the selection connectors 66, 67, 68, 69, 70, 71, 72 and 73 communicated with the common connector 74 according to signals of the control module 2; and 64 refers to a four-position selection valve group;

18-1 refers to a front pressing structure of the reactor, and 18-2 refers to a rear pressing structure of the reactor;

91 refers to a rotating shaft of the pressing part, and the pressing part 18 is fixed to the reactor frame 15 through the rotating shaft and can rotate around the rotating shaft;

96 refers to a reactor upper cover; and 99 refers to a connecting shaft of the reactor upper cover 96 and the reactor frame 15;

106 refers to an inner wall of the reactor 14; 107 refers to a reactant; and 109 refers to a liquid flow indicator; and

112 refers to a fast card A; 113 refers to a fast card B; 114 refers to a pagoda connector of a fast card B113, which is a derivative part of 125, used to connect pipelines or is directly connected to a container wall; 125 refers to a closure member of the fast card B113, and forms a containing cavity with 116; 118-114 refers to an internal flow channel; 115 refers to an inner pagoda pattern of the fast card B113 and is used to prevent internal leakage and falling after the fast card A and the fast card B are assembled; 116 refers to a main body of the fast card B113; 117 refers to a conductor; 119 refers to an internal flow channel of the conductor; 120 refers to a guide structure of the fast card B113 and is combined with the fast card A for internal guide fixation; 121 refers to a limiting structure of the conductor and is used to prevent the conductor 117 from falling off the fast card B113; 122 refers to an inner limiting structure of the fast card B113 and is used to limit the backward distance of the conductor 117; 124 refers to an outer limiting structure of the fast card B113 and is used to limit the outward distance of the conductor 117; 123 refers to a structural part with one-way valve functions and is used to control that when the fast card B113 is separated from the fast card A112, the fast card B is blocked in a direction from 118 to 119 and communicated in a direction from 119 to 118; 129 refers to an upper blocking structure of the fast card A112 and is used to fix a leakproof ring 130; 130 refers to the leakproof ring of the fast card A112; 128 refers to a main body of the fast card A112; 127 refers to a lower blocking structure of the fast card A112; 126 refers to a pagoda connector of the fast card A112; 131 refers to a guide structure of the fast card A112; 132-126 refers to an internal flow channel; 133 refers to a structural part with one-way valve functions and is used to control that when the fast card B113 is separated from the fast card A112, the fast card A is blocked in a direction from 132 to 129 and communicated in a direction from 129 to 132; and when the fast card A and the fast card B are combined, the conductor 119 moves backward to 122 to open 123 of 113, so as to make the 113 lose the one-way valve functions, and 119 is inserted into 123 of 112, so as to make the 112 lose the one-way valve functions.

DETAILED DESCRIPTION

The present disclosure provides a biological reaction apparatus and a method for performing biological detection on basis of the apparatus. Modifications can be made by those skilled in the art by appropriately changing process parameters on basis of contents of the disclosure. It should be particularly pointed out that all similar substitutions and modifications are obvious to those skilled in the art and are all deemed to be included in the present disclosure. The method and application of the present disclosure are described by using exemplary embodiments. Apparently, a person skilled in the art may make changes, appropriate modifications, and combinations to the method and application described in this specification without departing from the content, spirit and scope of the present disclosure, to implement and apply the technologies of the present disclosure.

In view of shortcomings of the prior art, an objective of the present disclosure is to provide an automatic system used for reactions of biological macromolecules.

Another objective of the present disclosure is to provide a method for detecting biological macromolecules by using the automatic reaction system for biological macromolecules.

The objective of the present disclosure may be achieved by using the following technical solutions:

The present disclosure protects an automatic reaction system for biological macromolecules (can also be called a biological reaction apparatus in the present disclosure), including a power supply module 1, a control module 2, a liquid processing module 3, a reactor module 4 and a sensor 5; the power supply module 1 provides driving energy and energy required for reactions to the liquid processing module 3 and the reactor module 4; the liquid processing module 3 is controlled by the control module 2, and feeds back an operating state to the control module, and the liquid processing module 3 inputs or outputs a reactant to the reactor module 4; and the reactor module 4 feeds back an operating state to the control module 2 and the liquid processing module 3, the reactor module 4 can carry the reactant, and the reactant is suspended in the reactor module 4.

In some embodiments, the power supply module 1 includes a direct current power supply 6 and a switch 7; the control module 2 includes a system controller 8, an input device 9 and an output device 10; the liquid processing module 3 includes a valve 11 or a combination of valves 11, a pump 12 or a combination of pumps 12 and sample cells 13; the reactor module 4 includes a reactor 14; and the reactor 14 includes a reactor frame 15 and a reactor cavity 16 formed by the reactor frame 15; the power supply module 1 is separately connected to the control module 2, the liquid processing module 3 and the reactor module 4 through cables 25; the control module 2 is separately connected to the liquid processing module 3 and the reactor module 4 through the cables 25; the liquid processing module 3 is connected to the reactor module 4 through a pipeline 26; and the control module 2 is connected to the reactor module 4 through the sensor 5.

In some embodiments, the reactor module 4 utilizes liquid flow or gas flow to make the reactant suspended in the reactor 14. A liquid film or a gas film may be formed between the reactant and the wall of the reactor 14 to prevent a wall attachment effect of the reactant.

In some embodiments, there are one or more reactors 14, and the reactors can withstand a pressure.

In some embodiments, when there are a plurality of reactors 14, the reactors may be connected in series or in parallel.

In some embodiments, the reactor 14 may be a disposable reactor or a reusable reactor.

In some embodiments, at least one liquid inlet and outlet is formed in the reactor 14 and used for adding and discharging a reaction liquid.

In some embodiments, the inner wall of the reactor 14 is smooth or is provided with a certain structure, such as a diversion block 24, which is used to perform liquid diversion to make the liquid uniformly distributed in the reactor.

In some embodiments, the inner wall of the reactor 14 may be subjected to hydrophobization or hydrophilization treatment.

In some embodiments, hydrophobization may be one or more of siliconization and alkylation.

In some embodiments, hydrophilization may be one or more of hydroxylation, carboxylation and amination.

In some embodiments, the reactor frame 15 is further provided with a pressing part 18 to ensure the sealing performance after the reactor is closed.

In some embodiments, the reactor 14 is made from a metal material, such as stainless steel and aluminum alloy, or a polymer material, such as polypropylene and an acrylonitrile-styrene-butadiene copolymer.

In some embodiments, the reactor frame 15 is further provided with a sealing part 19, and the sealing part 19 is made from an elastic material or a material repellent to a reaction solution.

In some embodiments, the reactor module 4 further includes an identification module; and according to the biological reaction apparatus provided in the present disclosure, the type of the reactor and an existing program are fed back through identification results.

In some embodiments, RFID is used as the identification module. The reactor module 4 is provided with an identifier, and the reactor is provided with a serial number chip. After the reactor 14 is transferred into the reactor module 4, the serial number of the chip is identified by the identifier and has a corresponding program or no corresponding program in the reactor module 4. When there is an existing program, the program is called by the reactor module 4. When there is no corresponding program, a program may be set through the reactor module 4 and saved.

In some embodiments, a stopped reaction is continued by using an identification method. For example, after a reaction liquid is subjected to a reaction, the reactor 14 is removed from the reactor module 4 to stop the process. After the reactor 14 is put into the reactor module 4 again, an unfinished program is identified by the reactor module 4 and displayed on an interface, and a prompt about whether or not to continue the program is given to an operator.

In some embodiments, a mother liquid pool 23 is further included before the reactor 14, the reaction solution is diluted and removed by flowing through the mother liquid pool 23, and a final reaction solution is formed in the reactor 14.

In some embodiments, the reactant is a biological macromolecule vector, such as a thin film, polyacrylamide gel and agarose gel.

In some embodiments, when the reactant is a thin film, a micro-cavity is formed in the reactor 14. When the reactant is gel, the micro-cavity is the reactor cavity 16, and can withstand a positive pressure or a negative pressure.

In some embodiments, the liquid processing module 3 includes one or more sample storage containers, namely, the sample cells 13.

In some embodiments, the liquid processing module 3 includes at least one one-way and/or two-way pump 12.

In some embodiments, the pump 12 is one or more of a peristaltic pump, a diaphragm pump, a gear pump and a plunger pump.

In some embodiments, the reaction solution is pumped into or out of the reactor 14 by the pump 12.

In some embodiments, the liquid processing module 3 includes a valve 11 or a combination of valves 11.

In some embodiments, the valve 11 is one or more of a diaphragm valve, a pinch valve and a column valve.

In some embodiments, two or more different solutions in the reactor 14 may be used and automatically exchanged freely by the liquid processing module 3.

In some embodiments, the reactor 14 is connected to the liquid processing module 3 through a pipeline 26 or a one-way valve or a two-way fast connector. A two-way fast card is used to connect a pipeline and the reactor. When the reactor contains a liquid, the reactor is removed from the system (Example 17) and disconnected from the pipeline, and the reactor and the pipeline are blocked to prevent liquid leakage or contamination.

In some embodiments, the reaction liquid is cycled in the reactor 14 with the biological reaction apparatus using the pump 12.

In some embodiments, the biological macromolecule is one or more of nucleic acid, protein and polypeptide.

In some embodiments, the biological reaction apparatus includes a liquid sensing module.

In some embodiments, at least one reactor 14 is included. The number of reactors 14 depends on the number of samples in the reactor 14 and requirements of a reaction solution. For example, 1 sample and 1 solution require 1 reactor 14; 2 samples and 1 solution require 1 reactor 14. The sample is put into the reactor 14, and the system is operated according to settings after the solution quantity, sequence and time are set. In the biological reaction apparatus, the solution is pumped into or out of the reactor 14 through the pump 12, and a circulation may be formed according to requirements and settings to prolong the contact time of the sample and the reaction solution.

In some embodiments, the solution may be pumped by setting pulses to increase the contact chance.

Specifically, the structure of the automatic reaction system for biological macromolecules provided in the present disclosure is as follows:

FIG. 1 shows basic compositions of the present disclosure.

1 refers to a power supply module, including a direct current power supply 6 and a switch 7, and is used to convert alternative current input into direct current output and provide energy required for operation of other parts of the present disclosure.

2 refers to a control module, including a system controller 8, an input device 9 and an output device 10, and is operated with energy input from the power supply module 1; the energy provided by the power supply module 1 is transmitted to the liquid processing module 3 and the reactor module 4 through cables 25; and the working state of the liquid processing module 3 and the reactor module 4 is detected through the sensor 5 and controlled.

3 refers to a liquid processing module and includes a valve 11 or a combination of valves, a pump 12 or a combination of pumps and sample cells 13, and the valve 11 or the combination of valves, the pump 12 or the combination of pumps and the reactor 14 are connected through a pipeline (26). The valve 11 or the combination of valves performs sample selection according to signals of the control module 2, and the pump 12 or the combination of pumps moves the sample into or out of the reactor 14. The sensor 5 is used to detect the operating state of the liquid processing module 3 and give feedback to the control module 2. The operating energy of the liquid processing module 3 is transmitted from the power supply module 1 by the control module 2, or may be directly provided by the power supply module 1.

4 refers to a reactor module, where 14 refers to a reactor, 17 refers to an opening formed in the reactor frame 15 and is a liquid inlet 17-1 or a liquid outlet 17-2, and a liquid is pumped into or out of the reactor 14 by the pump 12 or the combination of pumps connected to the opening 17 through a pipeline. The sensor 5 is used to detect the operating state of the reactor 14 and give feedback to the control module 2. The operating energy of the reactor module 4 is transmitted from the power supply module 1 by the control module 2, or may be directly provided by the power supply module 1.

Figure 2:
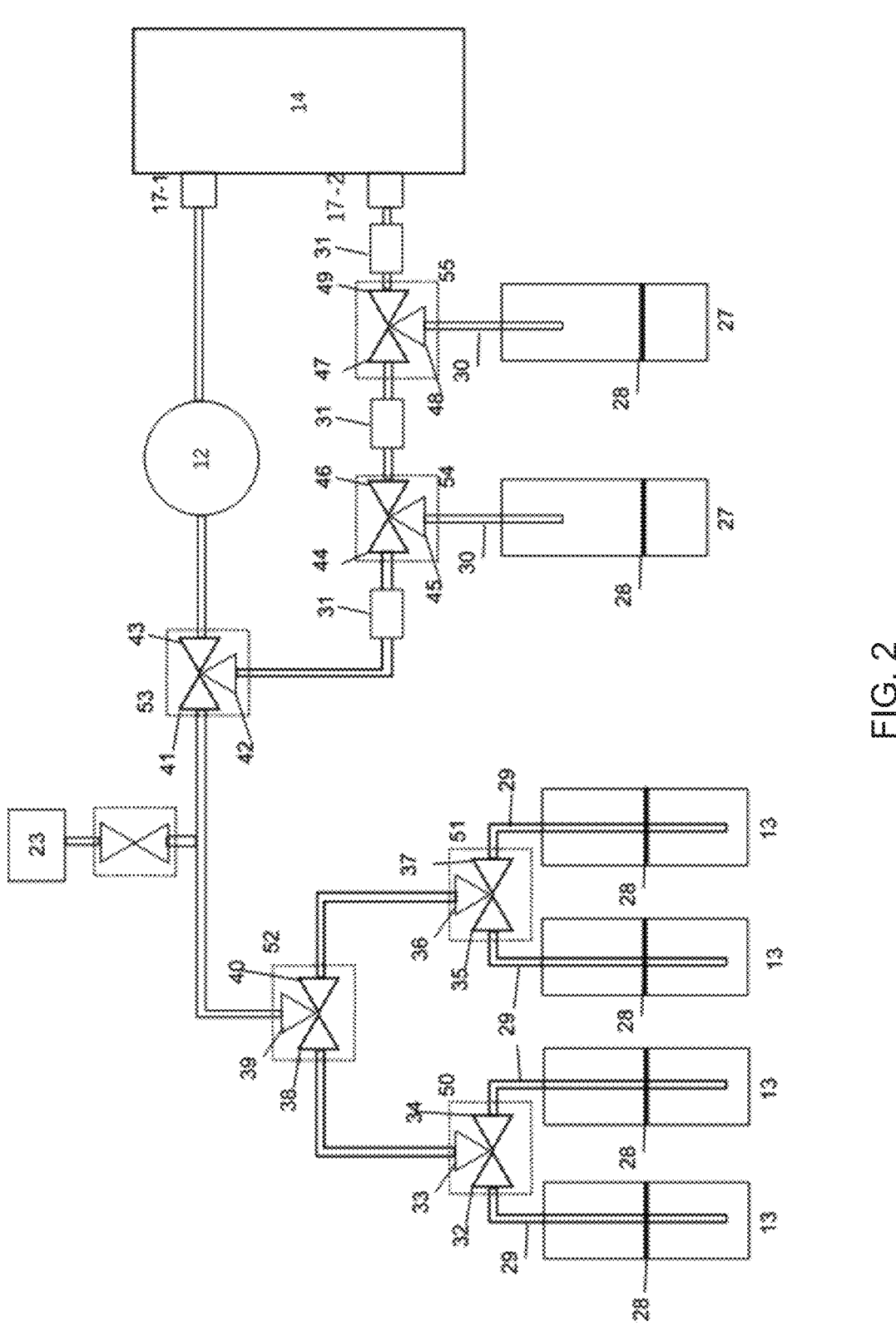
FIG. 2 is a schematic structural diagram of a biological reaction apparatus disclosed in Example 2 of the present disclosure.

FIG. 2 shows an application example of the present disclosure, which includes a reactor, four reaction liquids, 1 pump and 6 two-position three-way valves. 13 refers to four sample cells, and each sample cell 13 can be filled with a reaction liquid. 12 refers to a pump, specifically a peristaltic pump. 14 refers to a reactor. 17-1 refers to a liquid inlet. 17-2 refers to a liquid outlet. 23 refers to a mother liquid pool. 27 refers to a waste liquid collector. 28 refers to a liquid level indicator. 29 refers to a reaction liquid inlet and outlet pipeline. 30 refers to a waste liquid discharge or air inlet pipeline. 50, 51, 52, 53, 54 and 55 each refers to a two-position three-way valve. 32, 33 and 34 refer to three liquid receiving ports of a two-position three-way valve, 33 is a common end, and 32 and 33 are in normally open connection. 38, 39 and 40 refer to three liquid receiving ports of a two-position three-way valve, 39 is a common end, and 38 and 39 are in normally open connection. 35, 36 and 37 refer to three liquid receiving ports of a two-position three-way valve, 36 is a common end, and 35 and 36 are in normally open connection. 41, 42 and 43 refer to three liquid receiving ports of a two-position three-way valve, 43 is a common end, and 42 and 43 are in normally open connection. 44, 45 and 46 refer to three liquid receiving ports of a two-position three-way valve, 44 is a common end, and 46 and 44 are in normally open connection. 47, 48 and 49 refer to three liquid receiving ports of a two-position three-way valve, 49 is a common end, and 47 and 49 are in normally open connection. 28 needs to be maintained below the liquid level of a container to ensure that enough liquid may enter during operation. 30 needs to be maintained above the liquid level of a container to ensure that waste liquid is not sucked into a pipeline when gas is introduced. Furthermore, a gas-liquid selection valve may be added to the tail end of 30 to ensure that gas intake and liquid discharge are completely isolated.

Figure 3:
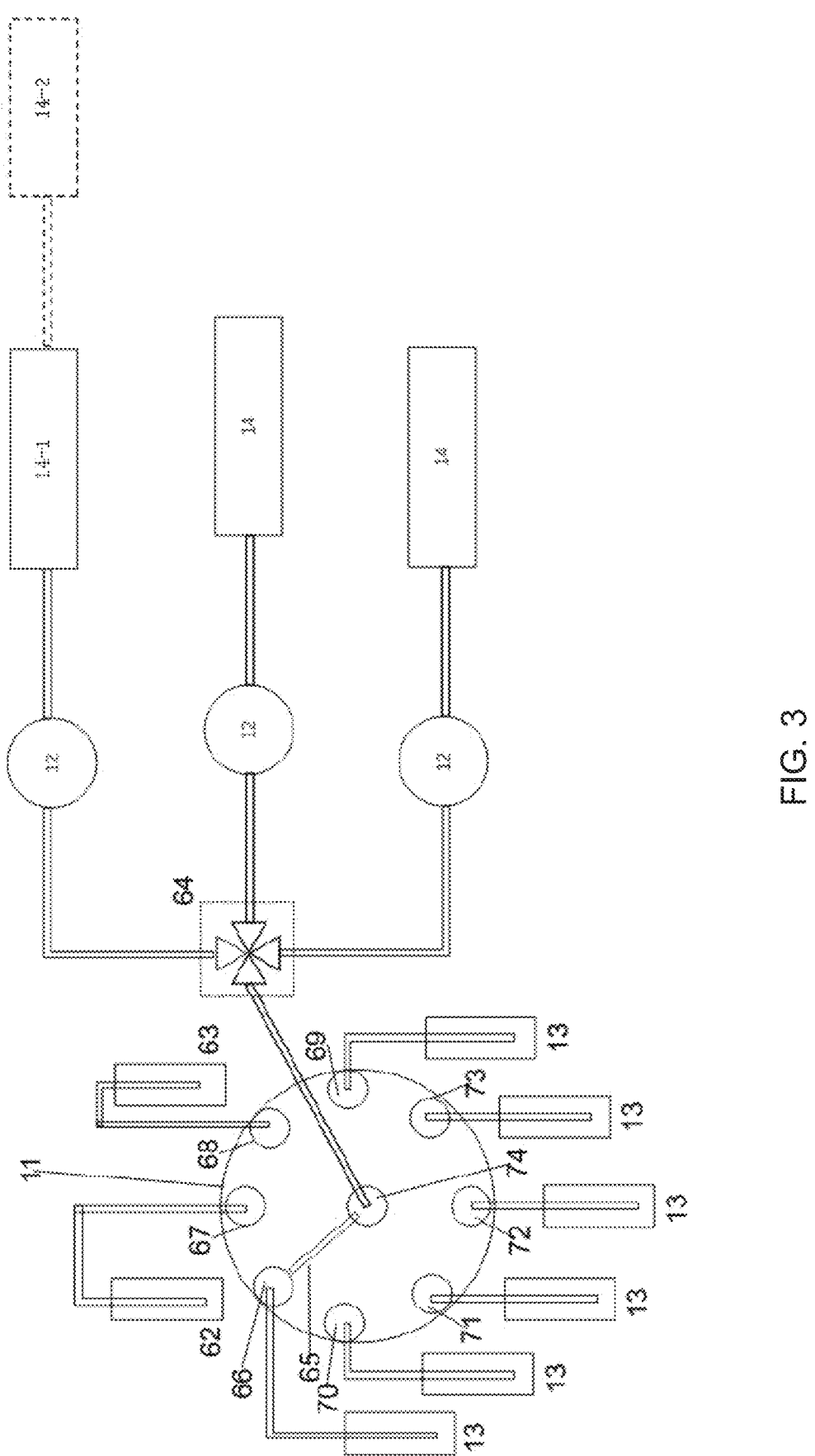
FIG. 3 is a schematic structural diagram of a biological reaction apparatus disclosed in Example 3 of the present disclosure.

FIG. 3 shows an application example of the present disclosure, which includes three reactors 14, six reaction liquids, three pumps 12 and two valves 11 or combinations of valves. 62 refers to a gas buffer bottle. 27 refers to a waste liquid collector. 13 refers to a sample cell. 11 refers to a valve, specifically an eight-position selection valve. 66, 67, 68, 69, 70, 71, 72 and 73 each refers to a selection connector of an eight-position valve. 74 refers to a common connector. 65 refers to a selection path, which is used to make the selection connectors 66, 67, 68, 69, 70, 71, 72 and 73 communicated with the common connector 74 according to signals of the control module 2. 64 refers to a four-position selection valve group. 12 refers to a pump, specifically a plunger pump. 14 refers to a reactor.

Figure 4:
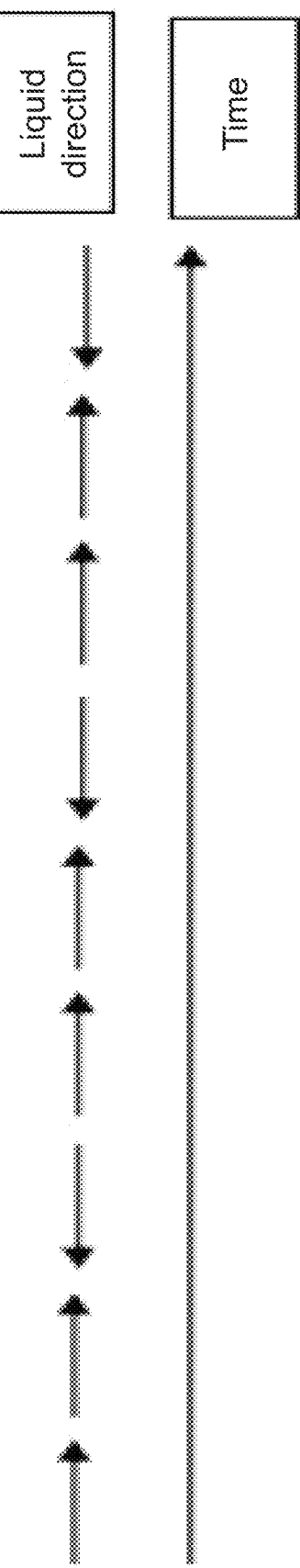
FIG. 4 shows a flow direction of a liquid in a reactor 14 on a time axis.

FIG. 4 shows a flow direction of a liquid in the reactor 14 on a time axis. Furthermore, the liquid stationary time may be prolonged to improve the effect.

Figure 5A:
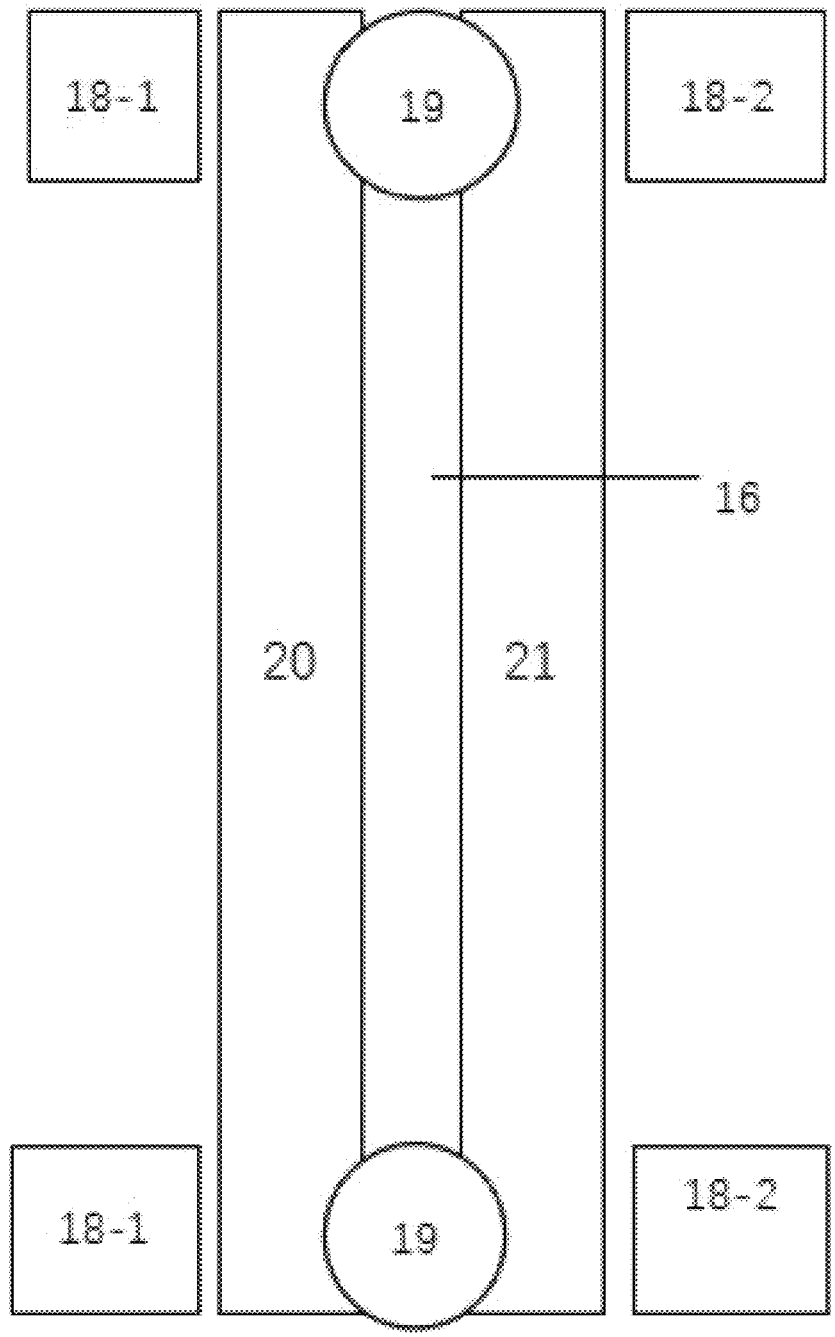
FIGS. 5(A)-5(G) show schematic structural diagrams of biological reaction apparatuses disclosed in Examples 4-6 of the present disclosure.

FIG. 5(A) is a schematic diagram of the reactor. 19 refers to a sealing part, 20 refers to a reactor front plate, 21 refers to a reactor rear plate, 18-1 refers to a front pressing structure of the reactor, and 18-2 refers to a rear pressing structure of the reactor. 18-1 and 20 may be one part, and 21 and 18-2 may be one part. After the reactor frame 15 of the reactor 14 is closed, a reactor cavity 16 can be formed. The size of the reactor cavity 16 may be determined by the sealing part 19 and a pressing part 18. When the reactant is a thin film, a micro-cavity is formed in the reactor cavity 16. Furthermore, a limiting part 22 may be added into 20 and 21 to maintain a certain cavity. Furthermore, the sealing part 19 may be omitted, and a sealing cavity is formed due to the tightness of 20 and 21. At least one opening 17 is formed in the reactor 14, 17-1 refers to a liquid inlet, and 17-2 refers to a liquid outlet; and the opening 17 is connected to the pump 12, the valve 11 or the reactor 14 and used for sample input or output.

Figure 5B:
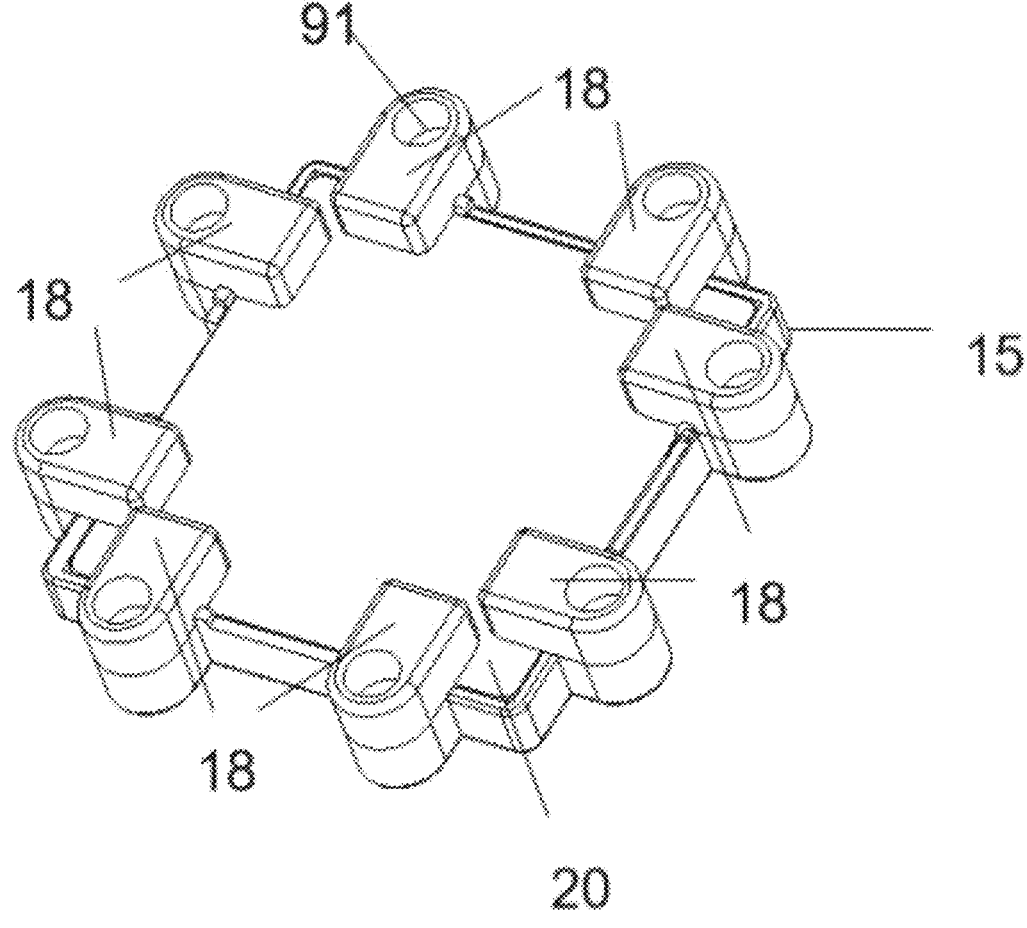
Figure 5C:
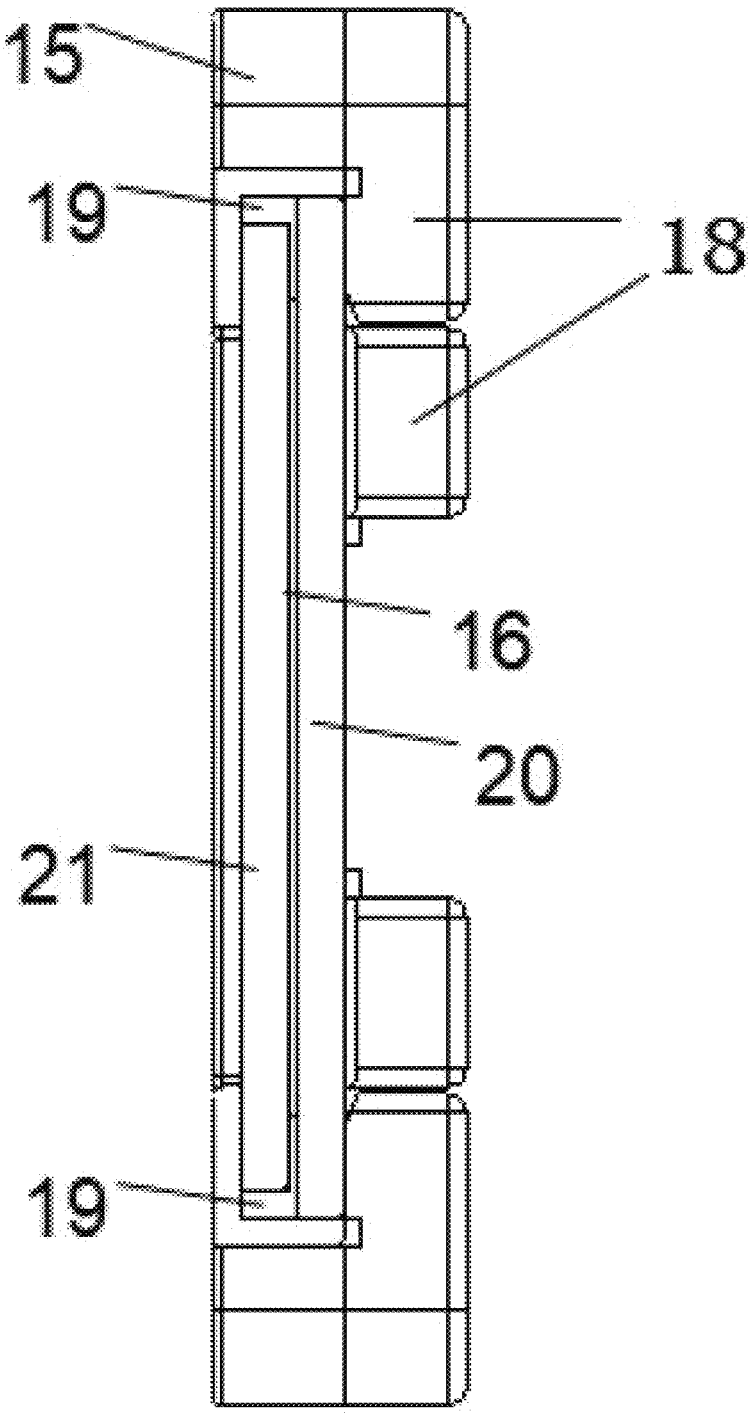
Figure 5D:
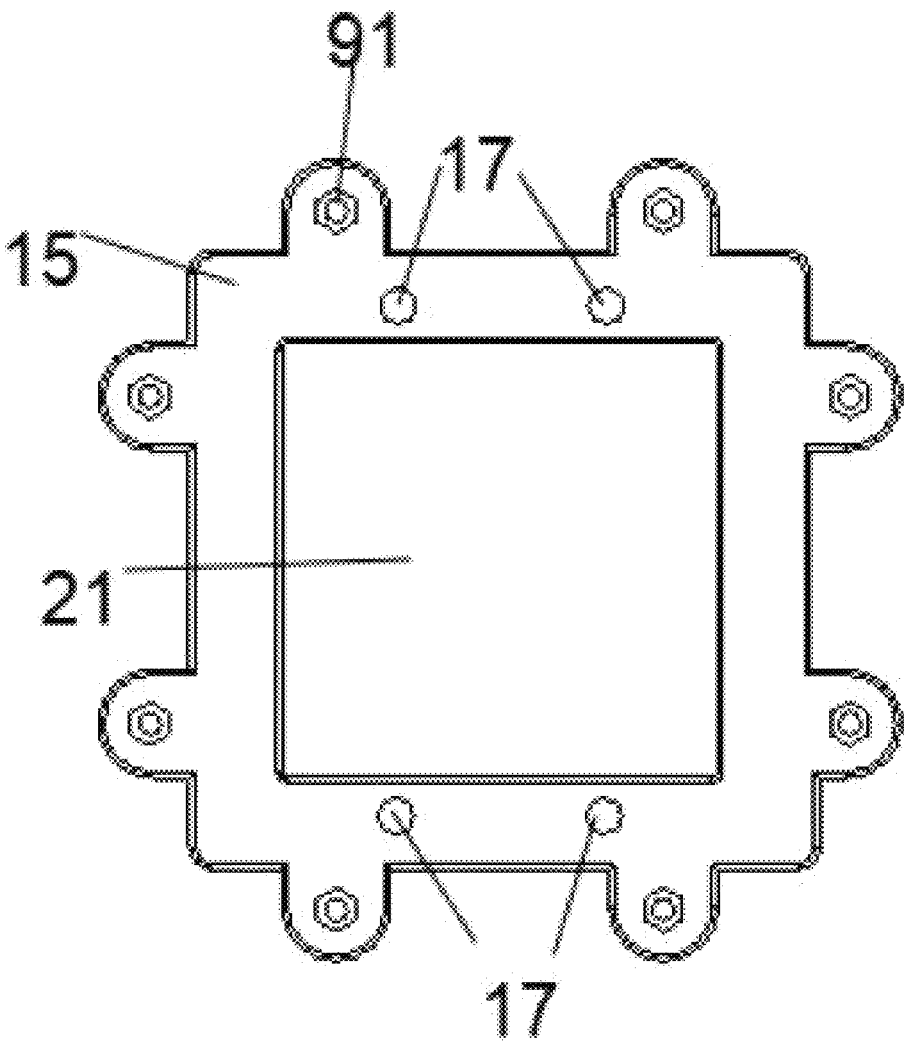

FIG. 5(B) shows a reactor design scheme, FIG. 5(C) is a cross-sectional view, and FIG. 5(D) is a rear view. 18 refers to a pressing part; 91 refers to a rotating shaft of the pressing part, and the pressing part 18 is fixed to the reactor frame 15 through the rotating shaft and can rotate around the rotating shaft; 20 refers to a reactor front plate; 21 refers to a reactor rear plate; 15 refers to a reactor frame; 17 refers to an opening, which is connected to the reactor rear plate 21 through the reactor frame 15; 19 refers to a sealing part; and 16 refers to a formed reactor cavity.

Figure 5E:
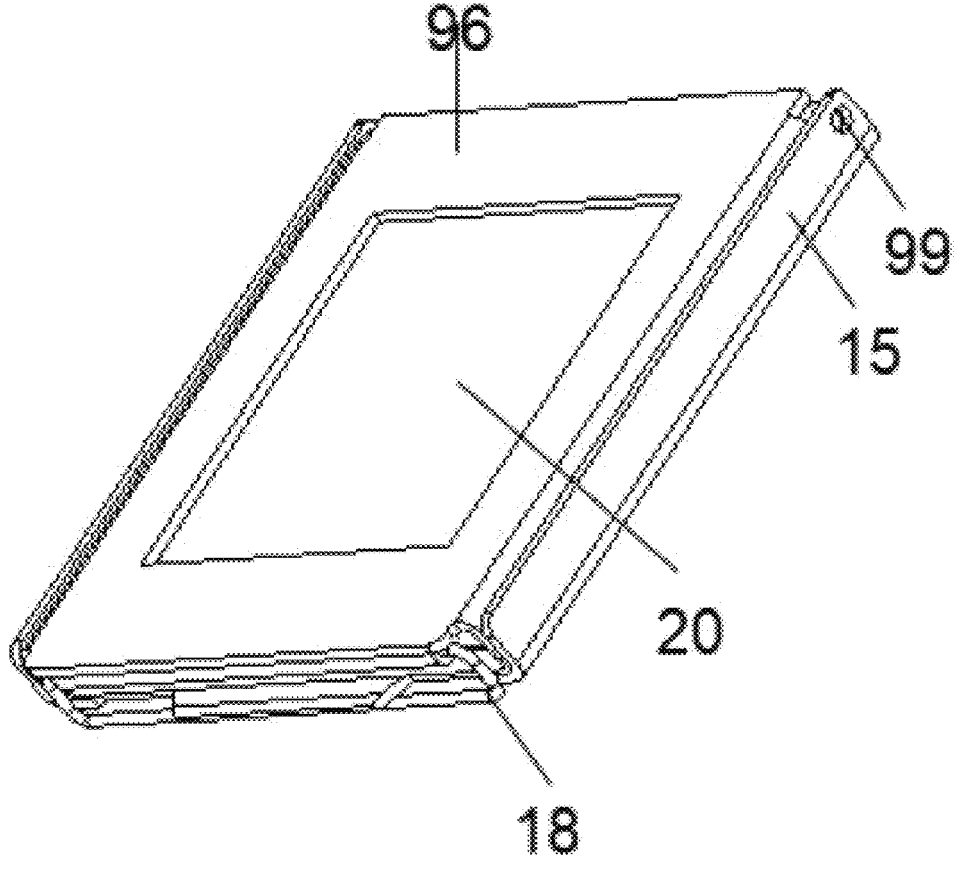
Figure 5F:
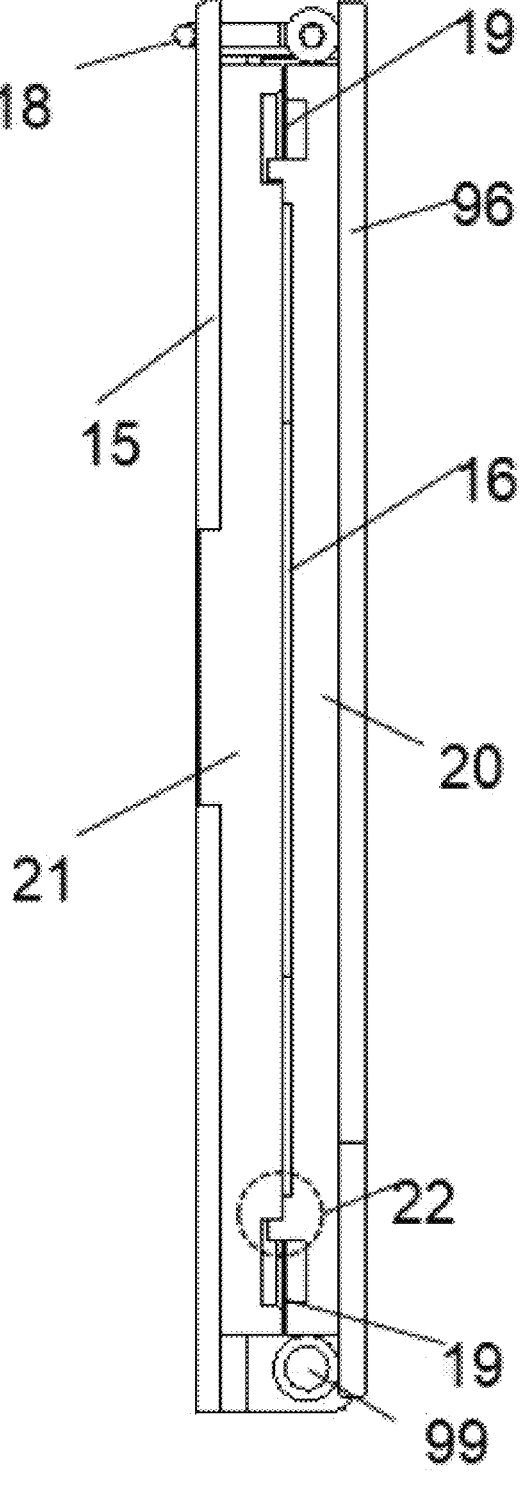
Figure 5G:
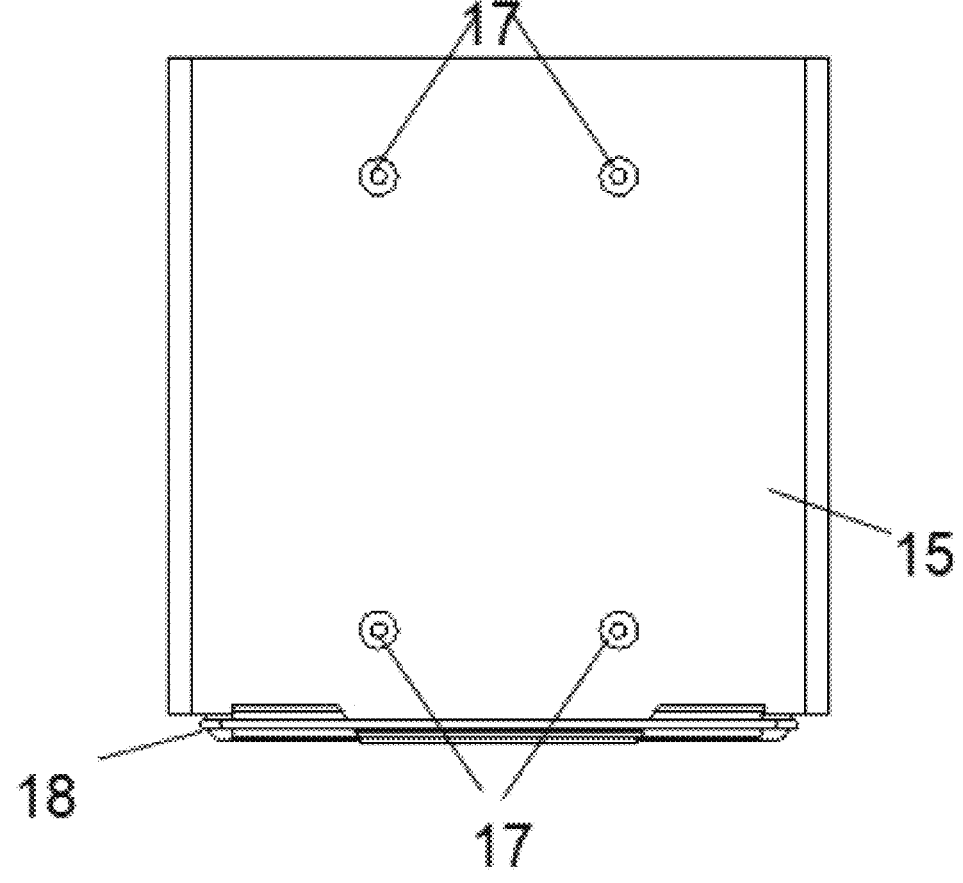

FIG. 5(E) shows a reactor design scheme, FIG. 5(F) is a cross-sectional view, and FIG. 5(G) is a rear view. 96 refers to a reactor upper cover; 15 refers to a reactor frame; 20 refers to a reactor front plate; 21 refers to a reactor rear plate; 99 refers to a connecting shaft of the reactor upper cover 96 and the reactor frame 15; 18 refers to a pressing part; 19 refers to a sealing part; 22 refers to a limiting part; 16 refers to a reactor cavity; and 17 refers to an opening.

Figure 6A:
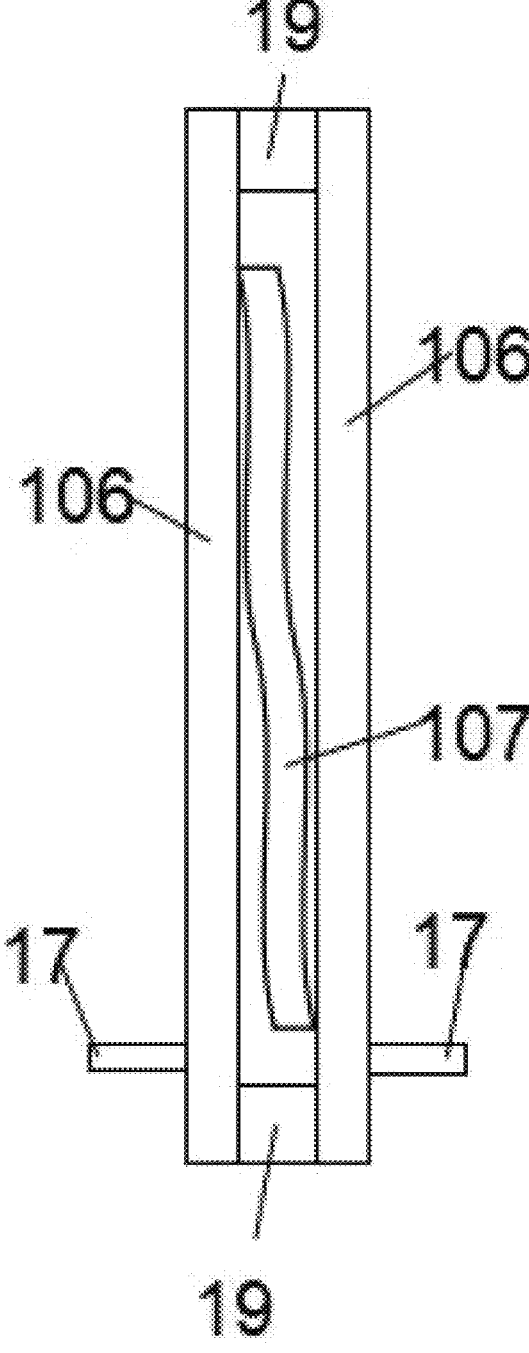
FIGS. 6(A)-6(C) show schematic structural diagrams of a biological reaction apparatus disclosed in Example 7 of the present disclosure.
Figure 6B:
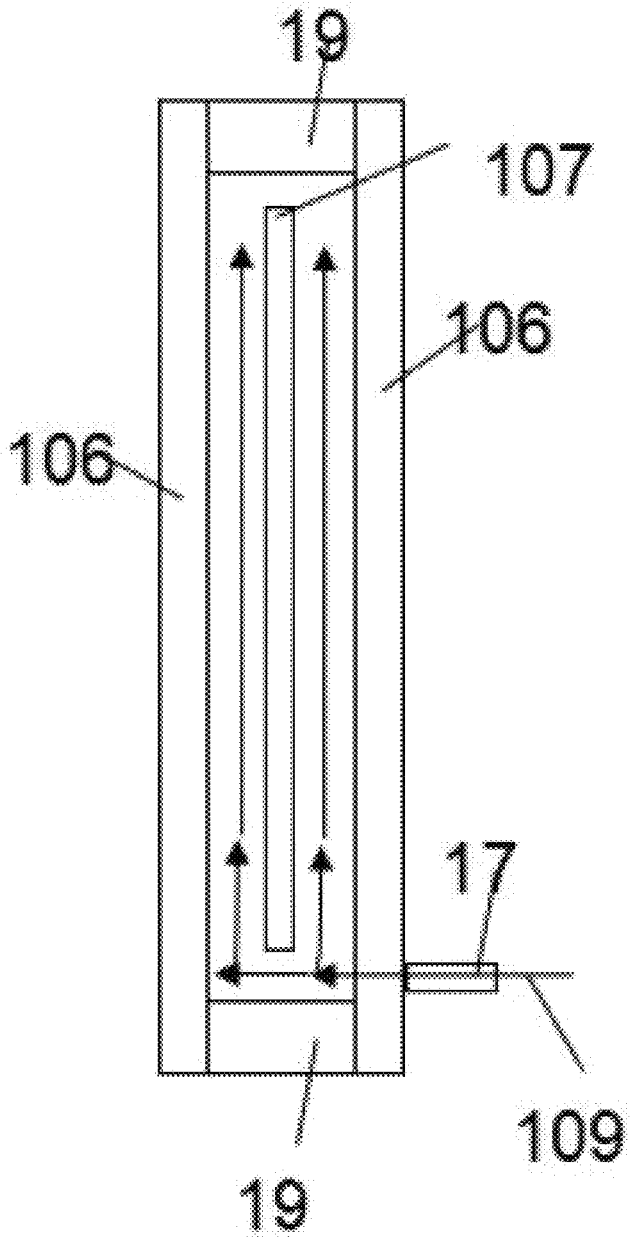
Figure 6C:
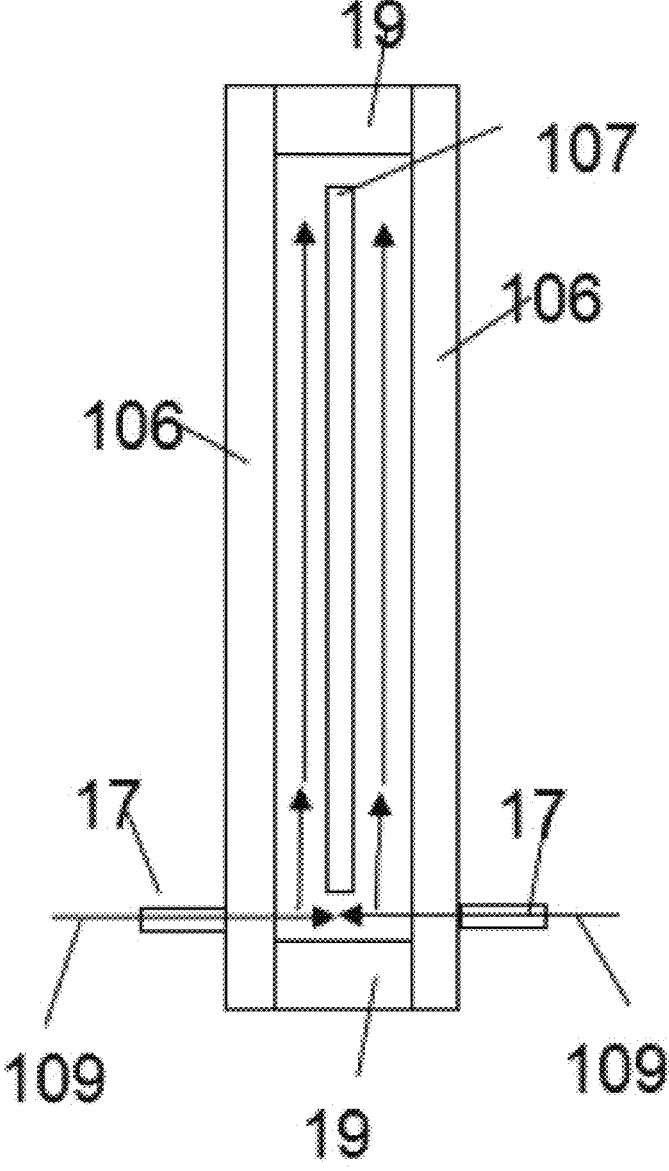

FIG. 6(A), FIG. 6(B) and FIG. 6(C) are shown, and 106 refers to an inner wall of the reactor 14. 17 refers to an opening. 107 refers to a reactant. 19 refers to a sealing part. 109 refers to a liquid flow indicator.

FIG. 6(A) shows the state of the reactant 107 unsuspended in the reactor 14, and the reactant is in an irregular shape and may be partially attached to the inner wall 106 of the reactor 14.

FIG. 6(B) and FIG. 6(C) are schematic diagrams of the reactant suspended in a liquid. After the liquid enters the reactor 14, the liquid flows through a gap between the reactant and the reactor 14 to make the reactant suspended in the reactor 14. The liquid is introduced through liquid inlets on both sides, and the reactant is suspended in the reactor 14 through the liquid flow. Furthermore, as shown in FIG. 6(B), the reactant is suspended by introducing a liquid on one side.

Figure 7:
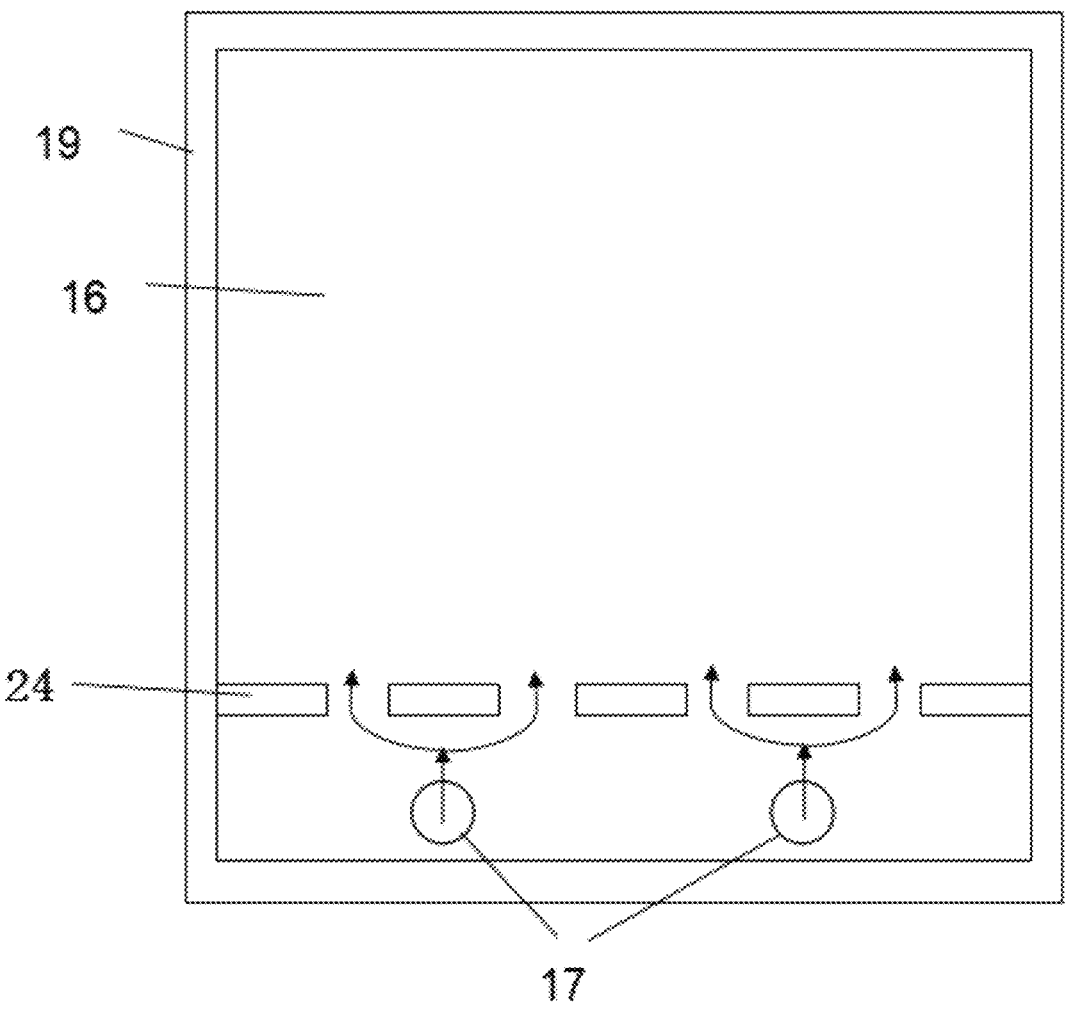
FIG. 7 is a schematic structural diagram of a biological reaction apparatus disclosed in Example 8 of the present disclosure.

FIG. 7 shows that the liquid flow is subjected to diversion by adding an opening 17 or a diversion block 24 to make the liquid entering the reactor 14 uniformly distributed. 17 refers to an opening and is specifically a liquid inlet; 19 refers to a sealing part and is specifically a sealing ring; 16 refers to a reactor cavity; and 24 refers to a diversion block in the reactor 14.

Figure 8A:
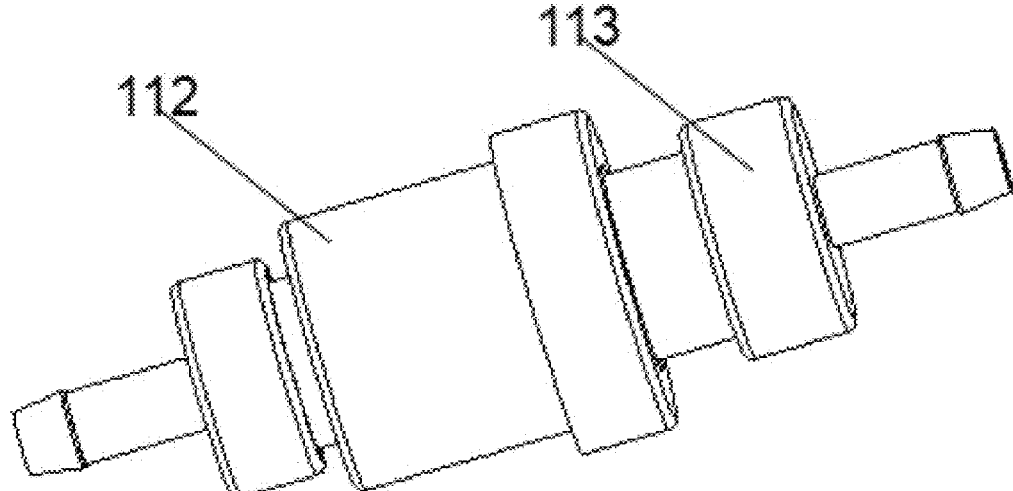
FIGS. 8(A)-8(E) show schematic structural diagrams of a biological reaction apparatus disclosed in Example 9 of the present disclosure; the biological reaction apparatus includes a two-way fast card.

FIG. 8(A) is a schematic diagram of a two-way fast card set consisting of a fast card A112 and a fast card B113; FIG.

US 12,680,068 B2

13

14

Figure 8B:
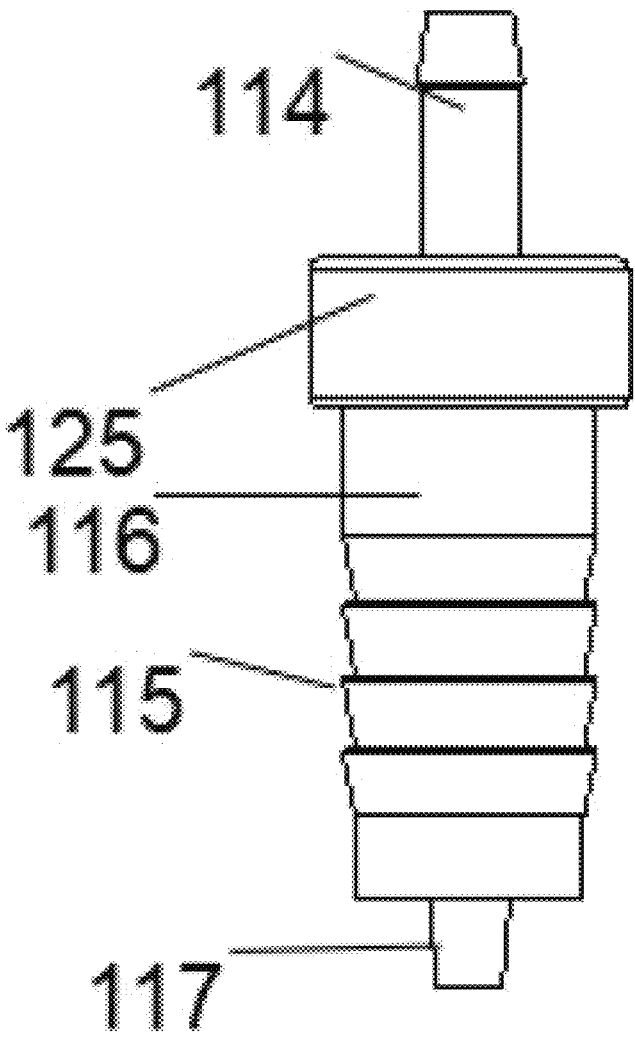
Figure 8C:
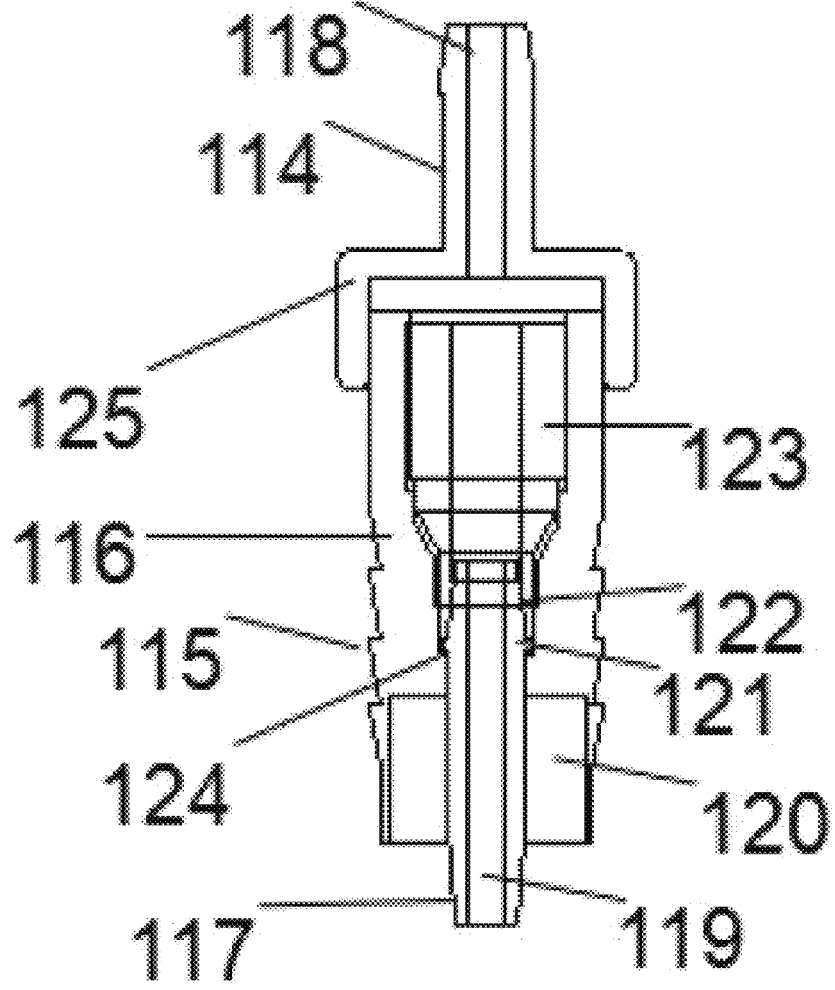
Figure 8D:
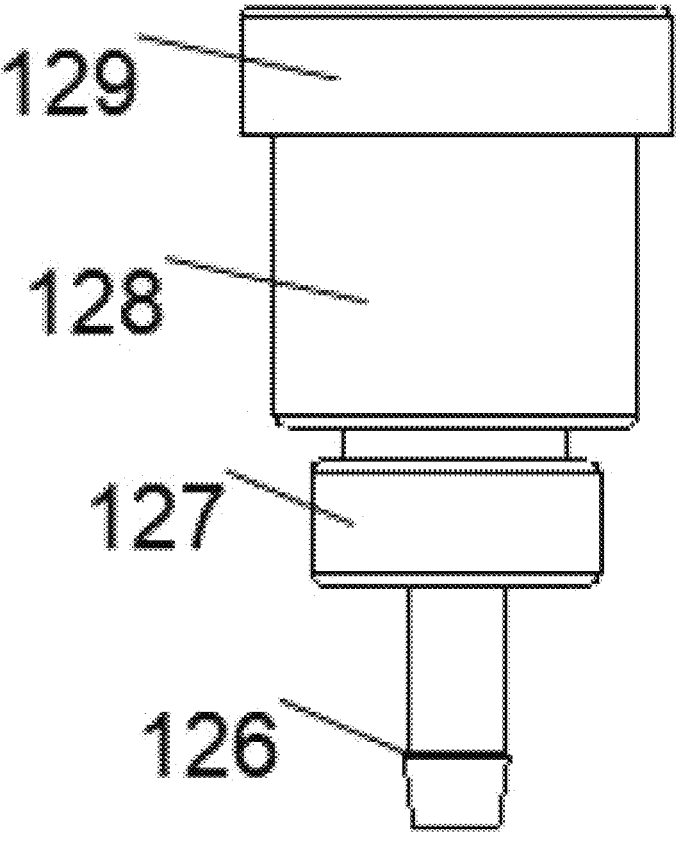
Figure 8E:
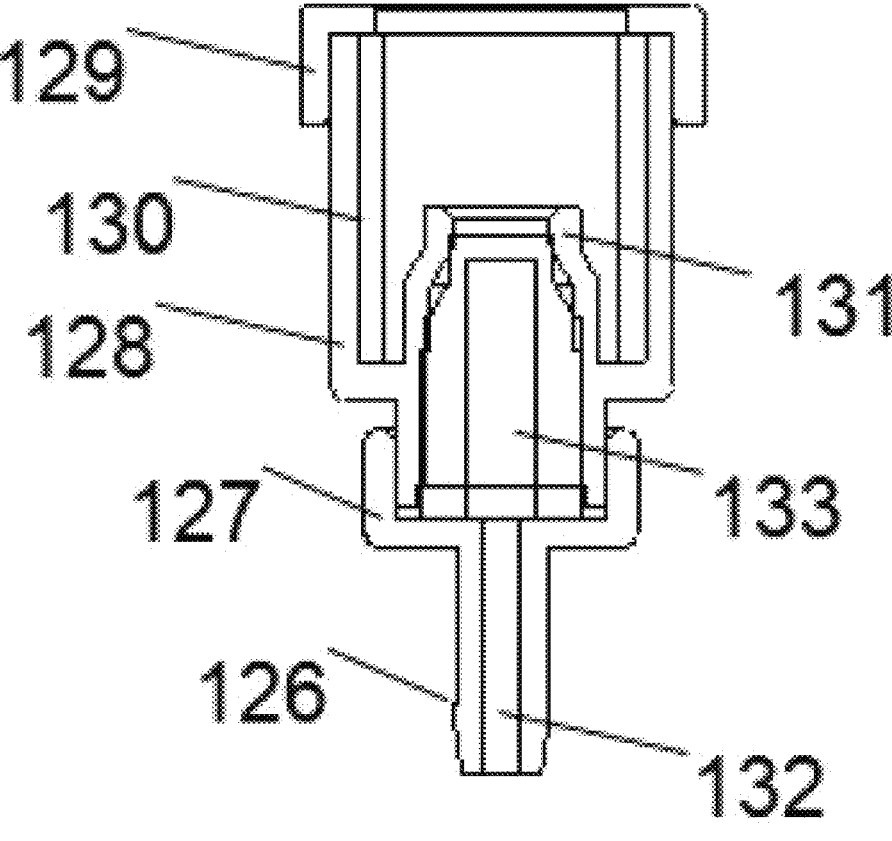

8(B) is a schematic diagram of the fast card B113; FIG. 8(C) is a cross-sectional view of the fast card B113; FIG. 8(D) is a schematic diagram of the fast card A112; FIG. 8(E) is a cross-sectional view of the fast card A112; 114 refers to a pagoda connector of the fast card B113, is a derivative part of 125, and is used to connect pipelines or is directly connected to a container wall; 125 refers to a closure member of the fast card B113, and forms a containing cavity with 116; 118 refers to an internal flow channel of 114; 115 refers to an inner pagoda pattern of the fast card B113 and is used to prevent internal leakage and falling after the fast card A and the fast card B are assembled; 116 refers to a main body of the fast card B113; 117 refers to a conductor; 119 refers to an internal flow channel of the conductor; 120 refers to a guide structure of the fast card B113 and is combined with the fast card A for internal guide fixation; 121 refers to a limiting structure of the conductor and is used to prevent the conductor 117 from falling off the fast card B113; 122 refers to an inner limiting structure of the fast card B113 and is used to limit the backward distance of the conductor 117; 124 refers to an outer limiting structure of the fast card B113 and is used to limit the outward distance of the conductor 117; 123 refers to a structural part with one-way valve functions and is used to control that when the fast card B113 is separated from the fast card A112, the fast card B is blocked in a direction from 118 to 119 and communicated in a direction from 119 to 118; 129 refers to an upper blocking structure of the fast card A112 and is used to fix a leakproof ring 130; 130 refers to the leakproof ring of the fast card A112; 128 refers to a main body of the fast card A112; 127 refers to a lower blocking structure of the fast card A112; 126 refers to a pagoda connector of the fast card A112; 131 refers to a guide structure of the fast card A112; 132 refers to an internal flow channel of 126; and 133 refers to a structural part with one-way valve functions and is used to control that when the fast card B113 is separated from the fast card A112, the fast card A is blocked in a direction from 132 to 129 and communicated in a direction from 129 to 132. When the fast card A and the fast card B are combined, the conductor 119 moves backward to 122 to open 123 of 113, so as to make the structural part lose the one-way valve functions, and 119 is inserted into 123 of 112, so as to make the structural part lose the one-way valve functions.

In another aspect, the present disclosure protects a method for detecting biological macromolecules by using the automatic reaction system for biological macromolecules.

The present disclosure has the following beneficial effects. Time is saved. The system is fully automatic, a lot of labors are reduced, and the efficiency is greatly improved. The sensitivity is high. Compared with the traditional method, the reaction efficiency is improved by liquid flow control, and thus the sensitivity is higher under conditions same as those in the traditional method. Reactor reagents are reduced. In the system, only a small amount of a liquid needs to be used in the reactor to complete a reaction requiring a large amount of reagents in the traditional method.

Raw materials and reagents used in the biological reaction apparatus and the method for performing biological detection on basis of the apparatus provided in the present disclosure can be purchased from the market.

The present disclosure is further described below with reference to the embodiments.

Example 1 Biological Reaction Apparatus Provided in the Present Disclosure

The present disclosure provides a biological reaction apparatus, as shown in FIG. 1, including a power supply module 1, a control module 2, a liquid processing module 3, a reactor module 4 and a sensor 5.

Where, 1 refers to a power supply module, including a direct current power supply 6 and a switch 7, and is used to convert alternative current input into direct current output and provide energy required for operation of other parts of the present disclosure.

2 refers to a control module, including a system controller 8, an input device 9 and an output device 10, and is operated with energy input from the power supply module 1; the energy provided by the power supply module 1 is transmitted to the liquid processing module 3 and the reactor module 4 through cables (25); and the working state of the liquid processing module 3 and the reactor module 4 is detected through the sensor 5 and controlled.

3 refers to a liquid processing module and includes a valve 11 or a combination of valves, a pump 12 or a combination of pumps and sample cells 13, and the valve 11 or the combination of valves, the pump 12 or the combination of pumps and a reactor 14 are connected through a pipeline (26). The valve 11 or the combination of valves performs sample selection according to signals of the control module 2, and the pump 12 or the combination of pumps moves a sample into or out of the reactor 14. The sensor 5 is used to detect the operating state of the liquid processing module 3 and give feedback to the control module 2. The operating energy of the liquid processing module 3 is transmitted from the power supply module 1 by the control module 2, or may be directly provided by the power supply module 1.

4 refers to a reactor module, where 14 refers to a reactor and includes a reactor frame 15 and a reactor cavity 16 formed by the reactor frame 15, 17 refers to an opening formed in the reactor frame 15 and is a liquid inlet 17-1 or a liquid outlet 17-2, and a liquid is pumped into or out of the reactor 14 by the pump 12 or the combination of pumps connected to the opening 17 through a pipeline. The sensor 5 is used to detect the operating state of the reactor 14 and give feedback to the control module 2. The operating energy of the reactor module 4 is transmitted from the power supply module 1 by the control module 2, or may be directly provided by the power supply module 1.

The power supply module 1 is separately connected to the control module 2, the liquid processing module 3 and the reactor module 4 through cables 25; the control module 2 is separately connected to the liquid processing module 3 and the reactor module 4 through the cables 25; the liquid processing module 3 is connected to the reactor module 4 through a pipeline 26; and the control module 2 is connected to the reactor module 4 through the sensor 5, and the opening 17 is connected to the pump 12 or the combination of pumps 12.

Example 2

On basis of the structure of the biological reaction apparatus provided in Example 1, the present disclosure further provides a biological reaction apparatus, as shown in FIG. 2, including a reactor, four reaction liquids, 1 pump and 6 two-position three-way valves.

13 refers to four sample cells, and each sample cell 13 can be filled with a reaction liquid. 12 refers to a pump, specifically a peristaltic pump. 14 refers to a reactor. 17-1 refers to a liquid inlet. 17-2 refers to a liquid outlet. 23 refers to a mother liquid pool. 27 refers to a waste liquid collector. 28 refers to a liquid level indicator. 29 refers to a reaction liquid inlet and outlet pipeline. 30 refers to a waste liquid discharge or air inlet pipeline. 50, 51, 52, 53, 54 and 55 each refers to a two-position three-way valve. 32, 33 and 34 refer to three liquid receiving ports of a two-position three-way valve, 33 is a common end, and 32 and 33 are in normally open connection. 38, 39 and 40 refer to three liquid receiving ports of a two-position three-way valve, 39 is a common end, and 38 and 39 are in normally open connection. 35, 36 and 37 refer to three liquid receiving ports of a two-position three-way valve, 36 is a common end, and 35 and 36 are in normally open connection. 41, 42 and 43 refer to three liquid receiving ports of a two-position three-way valve, 43 is a common end, and 42 and 43 are in normally open connection. 44, 45 and 46 refer to three liquid receiving ports of a two-position three-way valve, 44 is a common end, and 46 and 44 are in normally open connection. 47, 48 and 49 refer to three liquid receiving ports of a two-position three-way valve, 49 is a common end, and 47 and 49 are in normally open connection.

28 needs to be maintained below the liquid level of a container to ensure that enough liquid may enter during operation. 30 needs to be maintained above the liquid level of a container to ensure that waste liquid is not sucked into a pipeline when gas is introduced. Furthermore, a gas-liquid selection valve may be added to the tail end of 30 to ensure that gas intake and liquid discharge are completely isolated.

Example 3

On basis of the structure of the biological reaction apparatus provided in Example 1, the present disclosure further provides a biological reaction apparatus, as shown in FIG. 3, including three reactors 14, six reaction liquids, three pumps 12 and two valves 11 or combinations of valves.

62 refers to a gas buffer bottle. 27 refers to a waste liquid collector. 13 refers to a sample cell. 11 refers to a valve, specifically an eight-position selection valve. 66, 67, 68, 69, 70, 71, 72 and 73 each refers to a selection connector of an eight-position valve. 74 refers to a common connector. 65 refers to a selection path, which is used to make the selection connectors 66, 67, 68, 69, 70, 71, 72 and 73 communicated with the common connector 74 according to signals of the control module 2. 64 refers to a four-position selection valve group. 12 refers to a pump, specifically a plunger pump. 14 refers to a reactor. The reactors may be connected in series or in parallel. For example, the reactor 14-1 and the reactor 14-2 are connected in series.

Example 4

On basis of the structure of the biological reaction apparatus provided in Example 1, the present disclosure further provides a biological reaction apparatus, as shown in FIG. 5(A). 19 refers to a sealing part, 20 refers to a reactor front plate, 21 refers to a reactor rear plate, 18-1 refers to a front pressing structure of a reactor, and 18-2 refers to a rear pressing structure of the reactor. 18-1 and 20 may be one part, and 21 and 18-2 may be one part. After a reactor frame 15 of the reactor 14 is closed, a reactor cavity 16 can be formed. The size of the reactor cavity 16 may be determined by the sealing part 19 and a pressing part 18. When a reactant is a thin film, a micro-cavity is formed in the reactor cavity 16. Furthermore, a limiting part 22 may be added into 20 and 21 to maintain a certain cavity. Furthermore, the sealing part 19 may be omitted, and a sealing cavity is formed due to the tightness of 20 and 21. At least one opening 17 is formed in the reactor 14, 17-1 refers to a liquid inlet, and 17-2 refers to a liquid outlet; and the opening 17 is connected to a pump 12, a valve 11 or the reactor 14 and used for sample input or output.

Example 5

On basis of the structure of the biological reaction apparatus provided in Example 1, the present disclosure further provides a biological reaction apparatus, as shown in FIG. 5(B) to FIG. 5(D). 18 refers to a pressing part; 91 refers to a rotating shaft of the pressing part, and the pressing part 18 is fixed to a reactor frame 15 through the rotating shaft and can rotate around the rotating shaft; 20 refers to a reactor front plate; 21 refers to a reactor rear plate; 15 refers to the reactor frame; 17 refers to an opening, which is connected to the reactor rear plate 21 through the reactor frame 15; 19 refers to a sealing part; and 16 refers to a formed reactor cavity.

Example 6

On basis of the structure of the biological reaction apparatus provided in Example 1, the present disclosure further provides a biological reaction apparatus, as shown in FIG. 5(E) to FIG. 5(G). 96 refers to a reactor upper cover; 15 refers to a reactor frame; 20 refers to a reactor front plate; 21 refers to a reactor rear plate; 99 refers to a connecting shaft of the upper cover and a frame body; 18 refers to a pressing part; 19 refers to a sealing part; 22 refers to a limiting part; 16 refers to a reactor cavity; and 17 refers to an opening.

Example 7

On basis of the structure of the biological reaction apparatus provided in Example 1, the present disclosure further provides a biological reaction apparatus, as shown in FIGS. 6(A)-6(C). 106 refers to an inner wall of a reactor 14. 17 refers to an opening. 107 refers to a reactant. 19 refers to a sealing part. 109 refers to a liquid flow indicator.

FIG. 6(A) shows the state of the reactant 107 unsuspended in the reactor 14, and the reactant is in an irregular shape and may be partially attached to the inner wall 106 of the reactor 14.

FIG. 6(B) and FIG. 6(C) are schematic diagrams of the reactant suspended in a liquid.

After the liquid enters the reactor 14, the liquid flows through a gap between the reactant and the reactor 14 to make the reactant suspended in the reactor 14. The liquid is introduced through liquid inlets on both sides, and the reactant is suspended in the reactor 14 through the liquid flow. Furthermore, as shown in FIG. 6(B), the reactant is suspended by introducing a liquid on one side.

Example 8

On basis of the structure of the biological reaction apparatus provided in Example 1, the present disclosure further provides a biological reaction apparatus, as shown in FIG. 7. 17 refers to an opening and is specifically a liquid inlet; 19 refers to a sealing part and is specifically a sealing ring; 16 refers to a reactor cavity; and 24 refers to a diversion block in a reactor 14.

Example 9

On basis of the structure of the biological reaction apparatus provided in Example 1, the present disclosure further provides a biological reaction apparatus, as shown in FIGS.

8(A)-8(E). FIG. 8(A) is a schematic diagram of a two-way fast card set consisting of a fast card A112 and a fast card B113; FIG. 8(B) is a schematic diagram of the fast card B113; FIG. 8(C) is a cross-sectional view of the fast card B113; FIG. 8(D) is a schematic diagram of the fast card A112; and FIG. 8(E) is a cross-sectional view of the fast card A112; and 114 refers to a pagoda connector of the fast card B113, is a derivative part of 125, and is used to connect pipelines or is directly connected to a container wall; 125 refers to a closure member of the fast card B113, and forms a containing cavity with 116; 118 refers to an internal flow channel of 114; 115 refers to an inner pagoda pattern of the fast card B113 and is used to prevent internal leakage and falling after the fast card A and the fast card B are assembled; 116 refers to a main body of the fast card B113; 117 refers to a conductor; 119 refers to an internal flow channel of the conductor; 120 refers to a guide structure of the fast card B113 and is combined with the fast card A for internal guide fixation; 121 refers to a limiting structure of the conductor and is used to prevent the conductor 117 from falling off the fast card B113; 122 refers to an inner limiting structure of the fast card B113 and is used to limit the backward distance of the conductor 117; 124 refers to an outer limiting structure of the fast card B113 and is used to limit the outward distance of the conductor 117; 123 refers to a structural part with one-way valve functions and is used to control that when the fast card B113 is separated from the fast card A112, the fast card B is blocked in a direction from 118 to 119 and communicated in a direction from 119 to 118; 129 refers to an upper blocking structure of the fast card A112 and is used to fix a leakproof ring 130; 130 refers to the leakproof ring of the fast card A112; 128 refers to a main body of the fast card A112; 127 refers to a lower blocking structure of the fast card A112; 126 refers to a pagoda connector of the fast card A112; 131 refers to a guide structure of the fast card A112; 132 refers to an internal flow channel of 126; and 133 refers to a structural part with one-way valve functions and is used to control that when the fast card B113 is separated from the fast card A112, the fast card A is blocked in a direction from 132 to 129 and communicated in a direction from 129 to 132. When the fast card A and the fast card B are combined, the conductor 119 moves backward to 122 to open 123 of 113, so as to make the structural part lose the one-way valve functions, and 119 is inserted into 123 of 112, so as to make the structural part lose the one-way valve functions.

Example 10 Coomassie Brilliant Blue Staining

On basis of the biological reaction apparatus provided in Example 1, the present disclosure includes the following staining steps:

1: adding corresponding working solutions into reservoirs of a staining solution and a destaining solution;
2: putting to-be-stained gel or a film into a reactor;
3: setting a working procedure of an instrument:
setting the temperature to be 20-30° C., the area of a to-be-stained object to be 7.5*8 CM and the flow rate to be 40 ml/min;
A: introducing the staining solution (100 ml);
B: circulating the staining solution for 1 h;
C: discharging the staining solution;
D: introducing the destaining solution (100 ml);
E: circulating the destaining solution for 1 h;
F: discharging the destaining solution;
G: introducing the destaining solution (100 ml);
H: circulating the destaining solution for 1 h;

I: discharging the destaining solution; and
J: completing work of the instrument;
4: taking out the gel and recording results.

A traditional method includes the following staining process:

1: putting gel or a film into a box;
2: pouring 200 ml of a staining solution;
3: performing vibration at room temperature for 1 h;
4: removing the staining solution, and pouring 200 ml of a destaining solution;
5: performing vibration at room temperature for 1 h;
6: removing the destaining solution in step 4, and pouring 200 ml of a destaining solution;
7: performing vibration at room temperature for 1 h; and
8: repeating steps 6-7 until bands are clear and the background is clean.

Experimental samples include:

protein marker (genscript M00521), bovine serum albumin (BSA), *E. coli* cell lysis, mouse IgG and lysozyme.

The sample loading quantity is:

1: 5 μL of marker;
2: 20 μL of *E. coli* cell lysis;
3: 16 μL of *E. coli* cell lysis;
4: 12 μL of *E. coli* cell lysis;
5: 8 μL of *E. coli* cell lysis;
6: 4 μL of *E. coli* cell lysis;
7: 5 μL of marker;
8: 1000 ng of IgG, 1000 ng of BSA and 1000 ng of lysozyme;
9: 500 ng of IgG, 500 ng of BSA and 500 ng of lysozyme;
10: 250 ng of IgG, 250 ng of BSA and 250 ng of lysozyme;
11: 125 ng of IgG, 125 ng of BSA and 125 ng of lysozyme; and
12: 62.5 ng of IgG, 62.5 ng of BSA and 62.5 ng of lysozyme.

According to a staining formulation, the staining solution includes 0.1% of R250, 30% of ethanol, 10% of acetic acid and 60% of water; and the destaining solution includes 10% of ethanol, 10% of acetic acid and 80% of water.

Figure 9B:
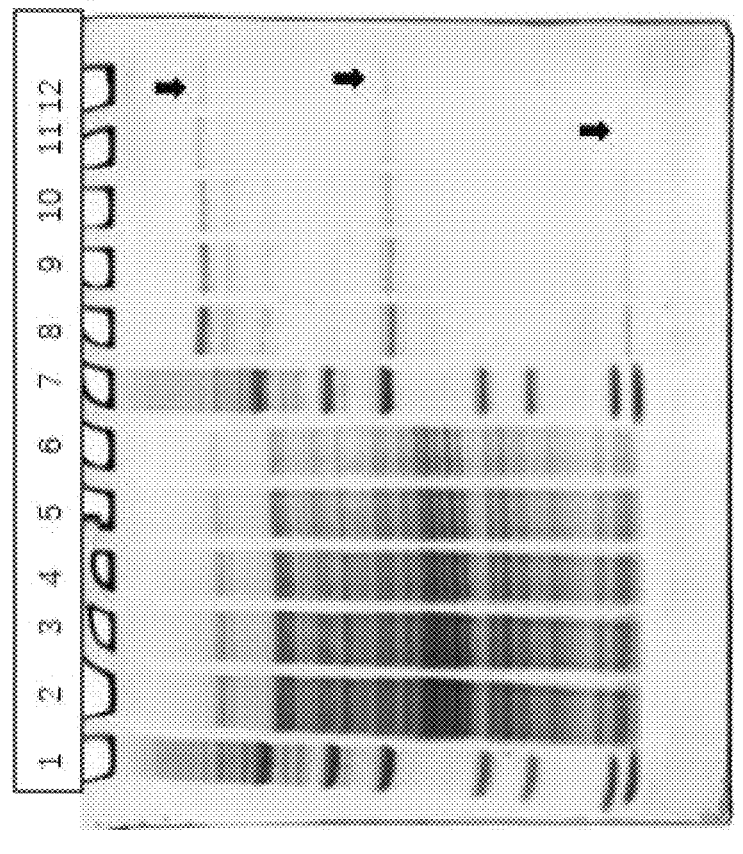
FIGS. 9(A)-9(E) show staining results of Example 10.
Figure 9A:
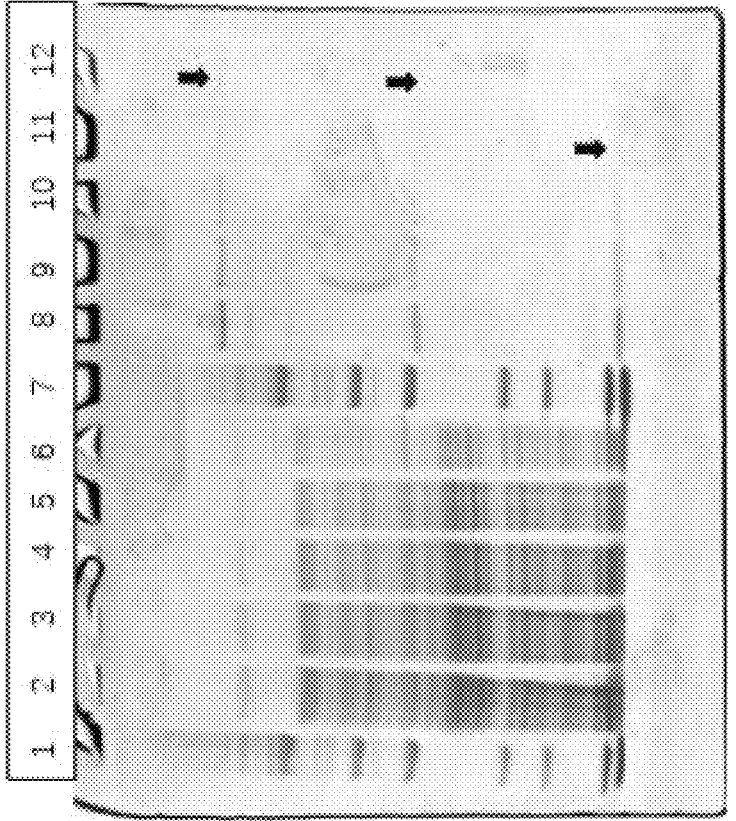
Figure 9C:
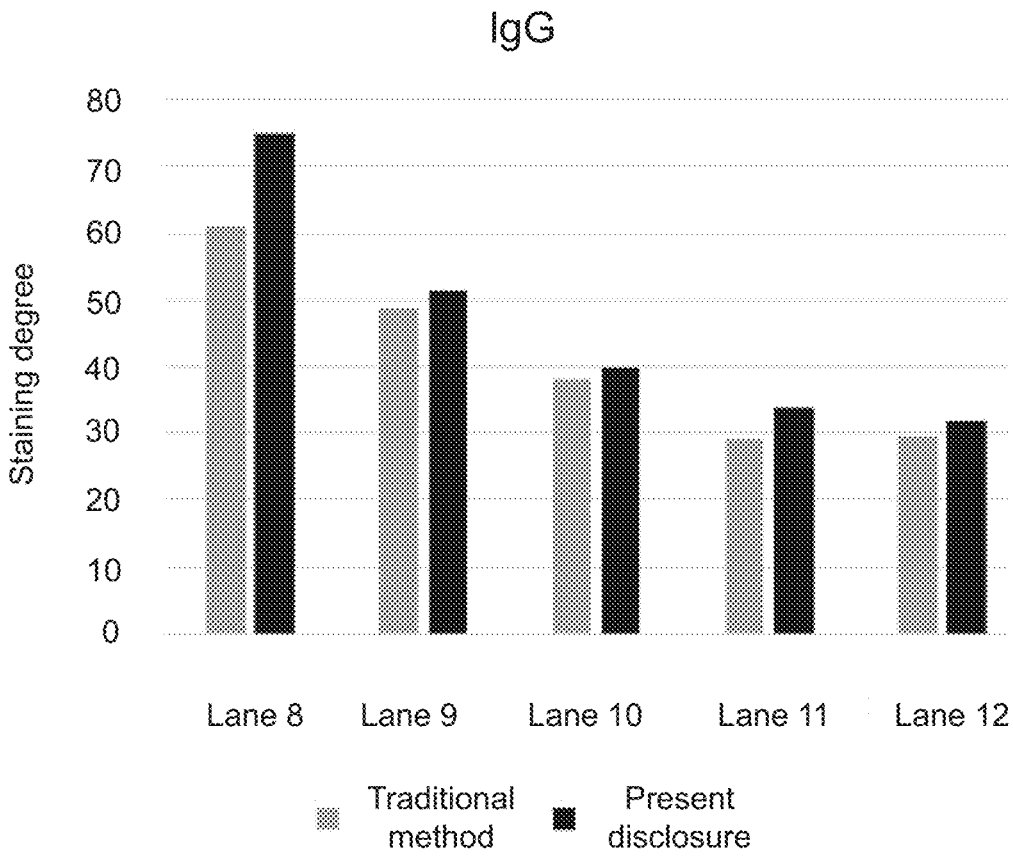
Figure 9D:
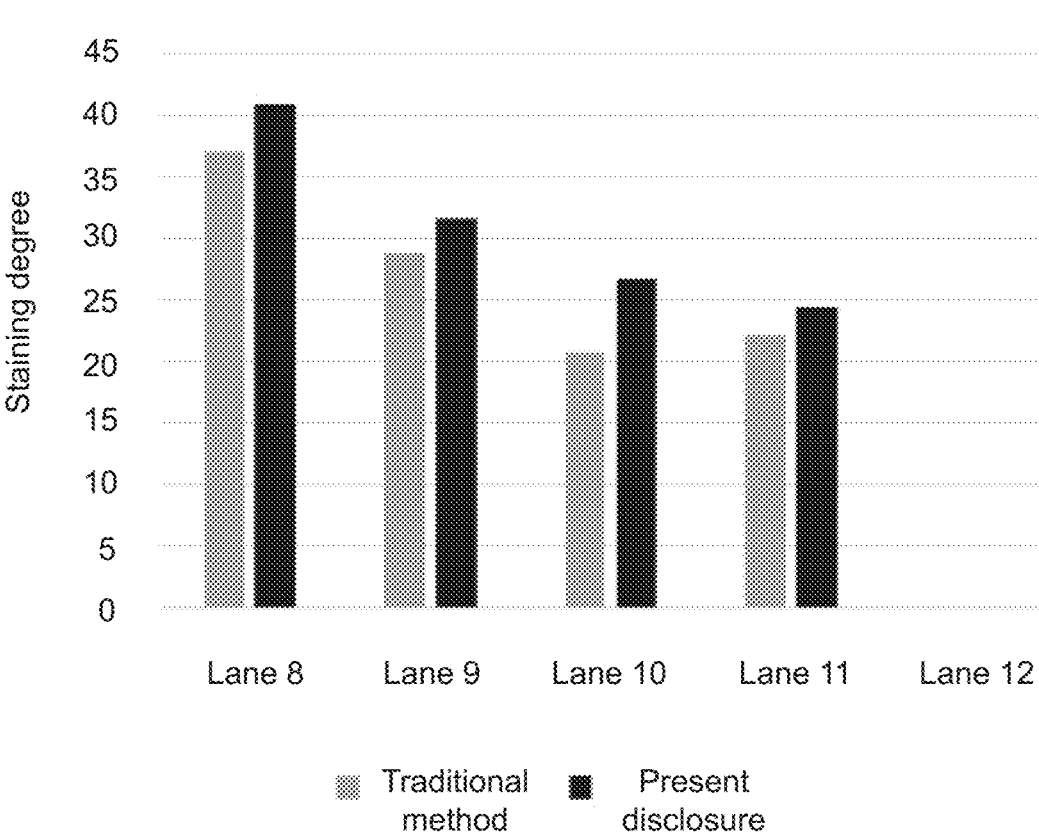
Figure 9E:
Figure 9E:
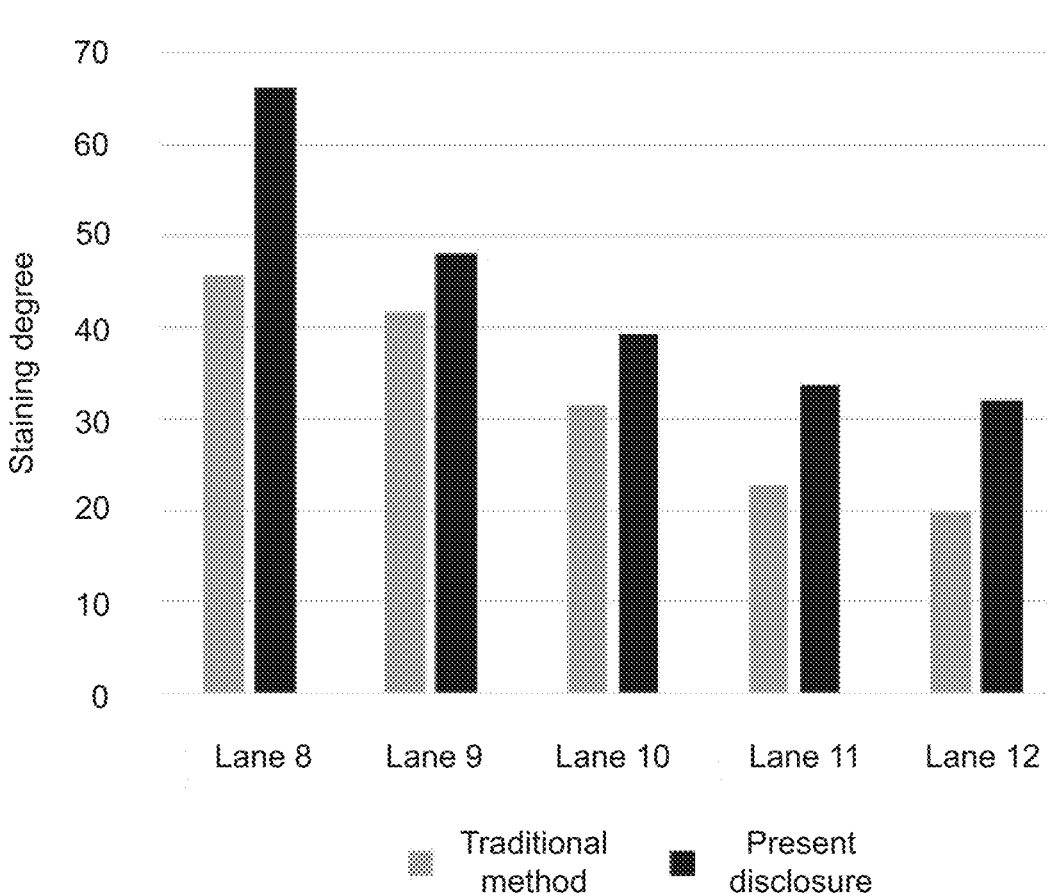

FIG. 9(A) shows staining results of the traditional method, FIG. 9(B) shows staining results of the present disclosure, and FIG. 9(C) shows comparative analysis of the staining degree of IgG in the staining results of the traditional method and the staining results of the present disclosure; FIG. 9(D) shows comparative analysis of the staining degree of lysozyme in the staining results of the traditional method and the staining results of the present disclosure; FIG. 9(E) shows comparative analysis of the staining degree of BSA in the staining results of the traditional method and the staining results of the present disclosure; and the results are shown on the same plane by using a bio-rad photosensitivity scanner.

When the traditional method is used for staining, a piece of gel requires at least 600 ml of a liquid for reaction. When the present disclosure is used, only 300 ml of a liquid is used to complete a reaction.

Result analysis:

TABLE 1

| | IgG | | BSA | | Lysozyme | | Mixed band | |
| --- | --- | --- | --- | --- | --- | --- | --- | --- |
| Lane | FIG. 9(A) | FIG. 9(B) | FIG. 9(A) | FIG. 9(B) | FIG. 9(A) | FIG. 9(B) | FIG. 9(A) | FIG. 9(B) |
| 8 | Visible | Visible | Visible | Visible | Visible | Visible | Visible | Visible |
| 9 | Visible | Visible | Visible | Visible | Visible | Visible | Visible | Visible |
| 10 | Visible | Visible | Visible | Visible | Visible | Visible | Invisible | Visible |
| 11 | Visible | Visible | Invisible | Visible | Invisible | Visible | Invisible | Visible |
| 12 | Visible | Visible | Invisible | Visible | Invisible | Invisible | Invisible | Invisible |

TABLE 2

| IgG | Traditional method | Present disclosure | Improvement of the present disclosure in comparison with the traditional method |
| --- | --- | --- | --- |
| Lane 8 | 60.7 | 74.6 | 22.90% |
| Lane 9 | 48.5 | 51.2 | 5.57% |
| Lane 10 | 37.9 | 39.6 | 4.49% |
| Lane 11 | 29.1 | 33.7 | 15.81% |
| Lane 12 | 29.5 | 31.6 | 7.12% |

TABLE 3

| BSA | Traditional method | Present disclosure | Improvement of the present disclosure in comparison with the traditional method |
| --- | --- | --- | --- |
| Lane 8 | 45.7 | 65.9 | 44.20% |
| Lane 9 | 41.7 | 47.9 | 14.87% |
| Lane 10 | 31.5 | 39.2 | 24.44% |
| Lane 11 | 22.7 | 33.7 | 48.46% |
| Lane 12 | 20 | 32 | 60.00% |

TABLE 4

| Lysozyme | Traditional method | Present disclosure | Improvement of the present disclosure in comparison with the traditional method |
| --- | --- | --- | --- |
| Lane 8 | 37.1 | 41 | 10.51% |
| Lane 9 | 28.8 | 31.6 | 9.72% |
| Lane 10 | 20.8 | 26.7 | 28.37% |
| Lane 11 | 22.2 | 24.4 | 9.91% |
| Lane 12 | 0 | 0 | — |

On IgG, all bands in the traditional method and the present disclosure are visible, but the color in the present disclosure is darker.

On BSA, the $10^{th}$ sample in the traditional method is visible, and all 12 samples in the present disclosure are visible, so that the sensitivity of the present disclosure is better.

On lysozyme, the $9^{th}$ sample in the traditional method is visible, and the $11^{th}$ sample in the present disclosure is visible, so that the sensitivity of the present disclosure is better.

It can be seen from FIG. 9(C), FIG. 9(D), FIG. 9(E) and Tables 2-4 that compared with the traditional method, the present disclosure has the advantages that the staining degree is increased by 4.49%-22.90% based on IgG detection results; the staining degree is increased by 14.87%-60.00% based on BSA detection results; and the staining degree is increased by 9.72%-28.37% based on lysozyme detection results.

In summary, compared with the traditional method, only 50% of reagents need to be used in the present disclosure, and the sensitivity and the staining degree of the present disclosure are better than those of the traditional method.

Example 11 Silver Staining

On basis of the biological reaction apparatus provided in Example 2, a reaction is introduced as follows:

a stationary liquid includes 40% of methanol, and each 200 ml of the stationary liquid includes 100 ul of formaldehyde;

a sensitizing agent includes 0.2 g/L of sodium thiosulfate;

a staining agent includes 20% of $AgNO_3$ and 250 ul/50 ml of $H_2O$; and a color developing solution includes 3% of sodium carbonate and 0.0004% L of sodium thiosulfate, and 25 ul of a formaldehyde solution/50 ml is added before use.

Experimental samples include:

protein marker (genscript M00521), E. coli cell lysis, mouse IgG and bovine serum albumin (BSA).

The sample loading quantity is:

1: 5 μL of marker;

2: 10 μL of E. coli cell lysis;

3: 8 μL of E. coli cell lysis;

4: 6 μL of E. coli cell lysis;

5: 4 μL of E. coli cell lysis;

6: 1 μL of E. coli cell lysis;

7: 5 μL of marker;

8: 100 ng of IgG and 100 ng of BSA;

9: 50 ng of IgG and 50 ng of BSA;

10: 25 ng of IgG and 25 ng of BSA;

11: 12.5 ng of IgG and 12.5 ng of BSA;

12: 6.25 ng of IgG and 6.25 ng of BSA; and

13: 3.125 ng of IgG and 3.125 ng of BSA.

The present disclosure includes the following steps:

1: putting gel into a reactor;

2: setting a program as follows:

setting the temperature to be 20-30° C. and the gel area to be 7.5*8 CM, where compared with Example 10, the reaction rate of silver staining reagents is lower than that of Coomassie brilliant blue, so that the flow rate needs to be reduced and is set to be 20 ml/min;

1) pumping in 100 ml of the stationary liquid, circulating the stationary liquid for 10 min and pumping out the stationary liquid after a reaction is completed;

2) pumping in 100 ml of ddH$_2$O, circulating the water for 5 min, pumping out the water and repeating to complete the step 2 times;

3) pumping in 100 ml of the sensitizing agent, circulating the sensitizing agent for 1 min and pumping out the sensitizing agent;

4) pumping in 100 ml of ddH$_2$O, circulating the water for 1 min, pumping out the water and repeating to complete the step 2 times;

5) pumping in 100 ml of the staining agent, circulating the staining agent for 10 min and pumping out the staining agent;

6) pumping in 100 ml of ddH$_2$O, circulating the water for 1 min, pumping out the water and repeating to complete the step 2 times;

7) pumping in 100 ml of the color developing solution, circulating the color developing solution for 10 min and pumping out the color developing solution; and 8) pumping in 100 ml of ddH$_2$O, circulating the water for 5 min and pumping out the water;

3: taking out the gel and recording results.

A traditional method includes the following steps:

1: putting gel into a container;

2: pouring 200 ml of a stationary liquid, performing vibration at room temperature for 10 min and discharging waste liquid;

3: pouring 200 ml of ddH$_2$O, performing vibration at room temperature for 5 min and discharging waste liquid;

4: repeating step 3;

5: pouring 200 ml of a sensitizing agent, performing vibration at room temperature for 1 min and discharging waste liquid;

6: pouring 200 ml of ddH$_2$O, performing vibration at room temperature for 1 min and discharging waste liquid;

7: repeating step 6;

8: pouring 200 ml of a staining agent, performing vibration at room temperature for 10 min and discharging waste liquid;

9: pouring 200 ml of ddH$_2$O, performing vibration at room temperature for 1 min and discharging waste liquid;

10: repeating step;

11: pouring 200 ml of a color developing solution, performing vibration at room temperature for 10 min and discharging waste liquid;

12: pouring 200 ml of ddH$_2$O, performing vibration at room temperature for 5 min and discharging waste liquid; and 13: taking out the gel and recording results.

Figures 10A, 10B:
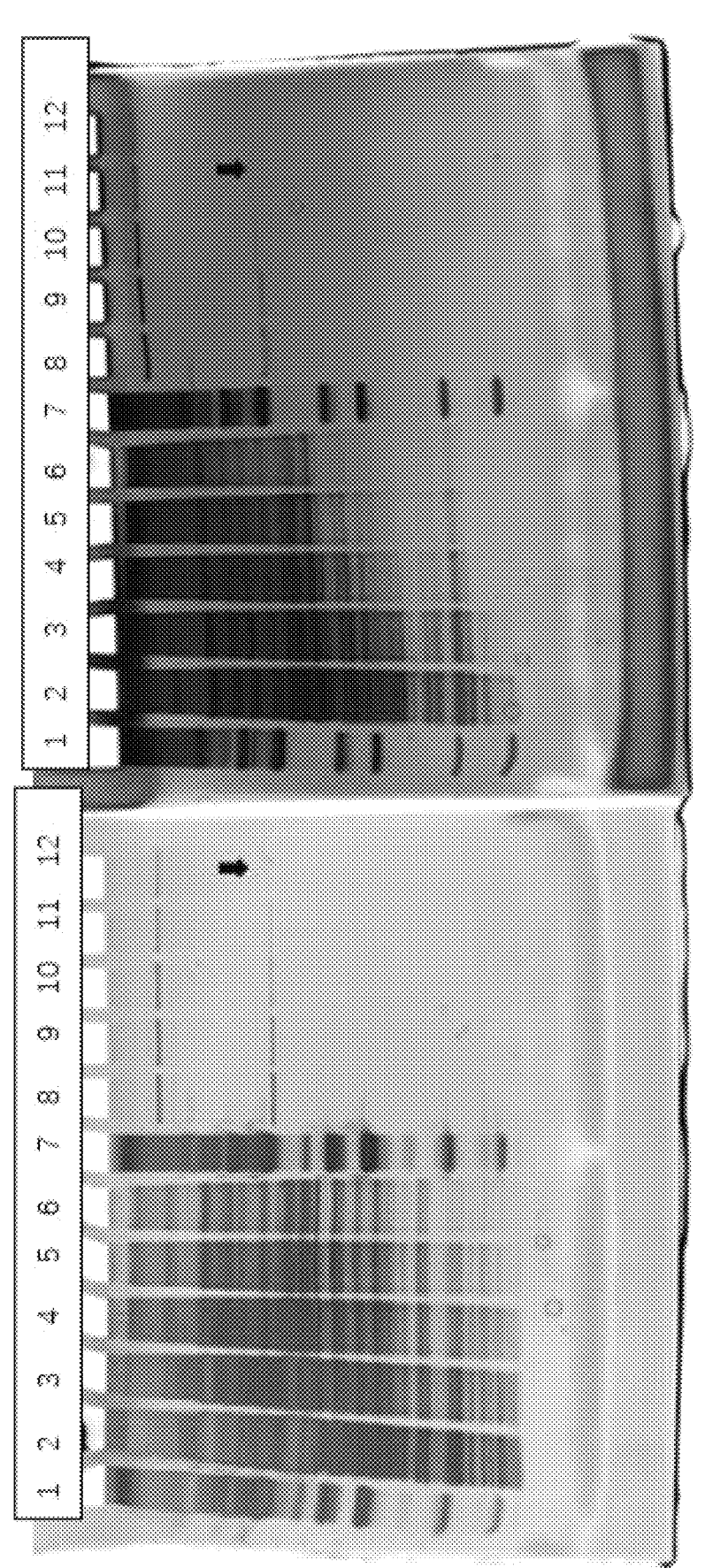
FIGS. 10(A)-10(D) show staining results of Example 11.
Figure 10C:
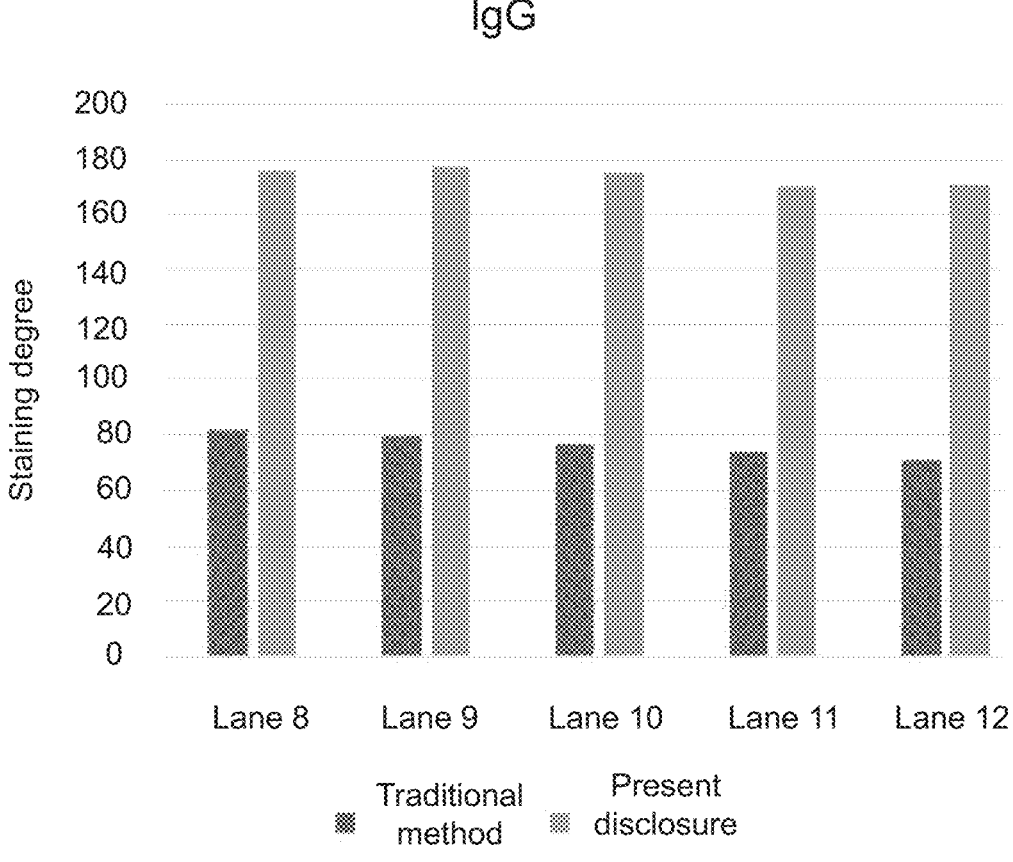
Figure 10D:
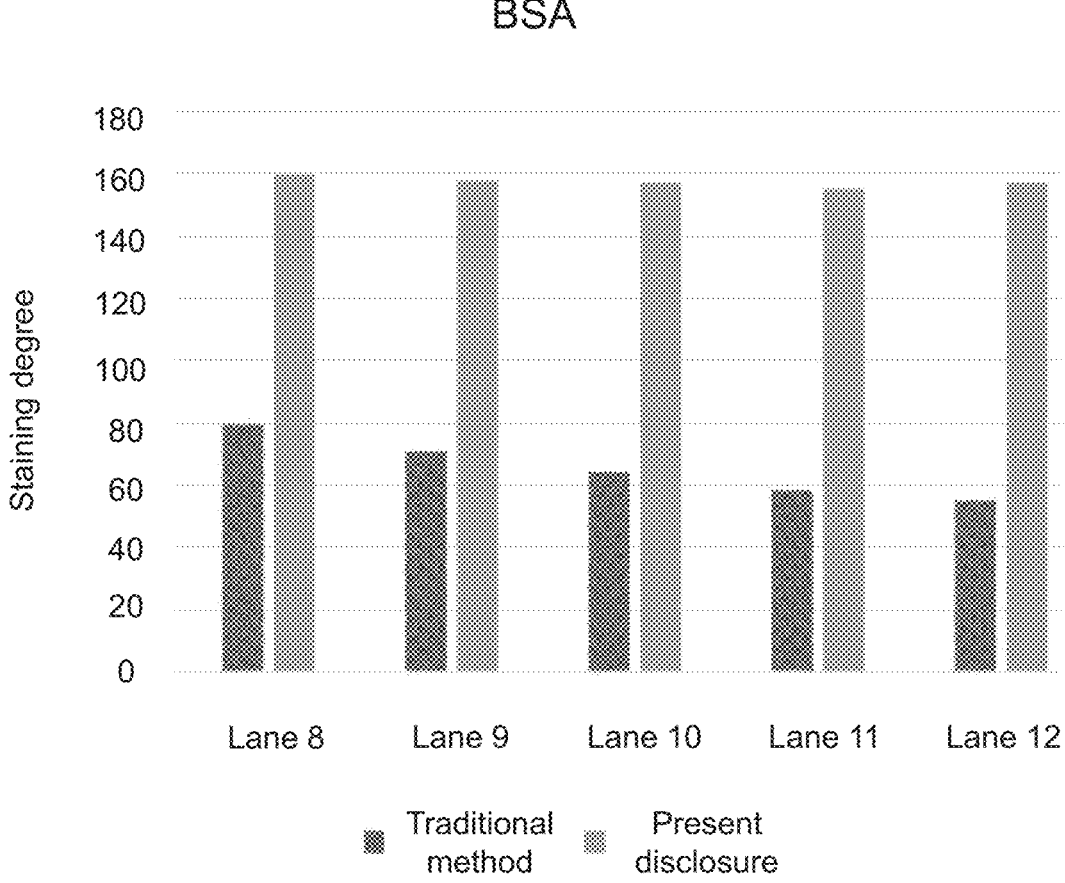

FIG. 10(A) shows staining results of the present disclosure; FIG. 10(B) shows staining results of the traditional method; FIG. 10(C) shows comparative analysis of the staining degree of IgG in the staining results of the traditional method and the staining results of the present disclosure; and FIG. 10(D) shows comparative analysis of the staining degree of BSA in the staining results of the traditional method and the staining results of the present disclosure.

TABLE 5

| | IgG | | BSA | |
|---|---|---|---|---|
| Lane | FIG. 10(A) | FIG. 10(B) | FIG. 10(A) | FIG. 10(B) |
| 8 | Visible | Visible | Visible | Visible |
| 9 | Visible | Visible | Visible | Visible |
| 10 | Visible | Visible | Visible | Visible |
| 11 | Visible | Visible | Visible | Invisible |
| 12 | Visible | Visible | Visible | Invisible |

TABLE 6

| IgG | Traditional method | Present disclosure | Improvement of the present disclosure in comparison with the traditional method |
|---|---|---|---|
| Lane 8 | 81.8 | 175.8 | 114.91% |
| Lane 9 | 79.5 | 177.3 | 123.02% |
| Lane 10 | 76.5 | 175 | 128.76% |
| Lane 11 | 74 | 169.6 | 129.19% |
| Lane 12 | 71.3 | 170.6 | 139.27% |

TABLE 7

| BSA | Traditional method | Present disclosure | Improvement of the present disclosure in comparison with the traditional method |
|---|---|---|---|
| Lane 8 | 79.3 | 159.3 | 100.88% |
| Lane 9 | 70.5 | 157.3 | 123.12% |
| Lane 10 | 63.7 | 156.8 | 146.15% |
| Lane 11 | 58 | 155.2 | 167.59% |
| Lane 12 | 54.7 | 156.7 | 186.47% |

It can be seen from the figures that when half of reagents are used, the sensitivity of the present disclosure is better than that of the traditional method, and the background is better than that of the traditional method. On IgG, all bands in the traditional method and the present disclosure are visible. On BSA, the 10$^{th}$ sample in the traditional method is visible, and all 12 samples in the present disclosure are visible, so that the sensitivity of the present disclosure is better.

It can be seen from FIG. 10(C), FIG. 10(D) and Tables 6-7 that compared with the traditional method, the method provided in the present disclosure has the advantages that the staining degree is increased by 114.91%-139.27% based on IgG detection results; and the staining degree is increased by 100.88%-186.47% based on BSA detection results.

In summary, compared with the traditional method, only 50% of reagents need to be used in the present disclosure, and the sensitivity and the staining degree are better than those of the traditional method.

Example 12 WB1

On basis of the biological reaction apparatus provided in Example 3, a reaction is introduced as follows:

proteins with His tags and the molecular weight of 93 kd and 7 kd are used as samples.

The sample loading quantity is:

1: 1 ul of WB Marker;

2: 150 ng of 93 kd protein and 10 ng of 7 kd protein;

3: 75 ng of 93 kd protein and 5 ng of 7 kd protein;

4: 37.5 ng of 93 kd protein and 2.5 ng of 7 kd protein;

5: 18.75 ng of 93 kd protein and 1.25 ng of 7 kd protein;

6: 9 ng of 93 kd protein and 0.6 ng of 7 kd protein;

7: 4.5 ng of 93 kd protein and 0.3 ng of 7 kd protein;

8: 2.25 ng of 93 kd protein and 0.15 ng of 7 kd protein;

9: 1 ng of 93 kd protein and 0.075 ng of 7 kd protein; and

10: 0.5 ng of 93 kd protein and 0.0375 ng of 7 kd protein.

A blocking solution includes 5% of skimmed milk powder and a PBS solution.

PBST is obtained by adding one thousandth of Tween 20 into PBS.

A primary antibody is mouse anti-His with a concentration of 1 mg/ml and is diluted with the blocking solution according to a ratio of 1:3000.

A secondary antibody is goat anti-mouse HRP with a concentration of 1 mg/ml and is diluted with the blocking solution according to a ratio of 1:10000.

The present disclosure includes the following steps:

1: putting two films back-to-back into a reactor and setting the temperature to be 20-30° C., the film area to be 7.5*8 CM*2 and the flow rate to be 40 ml/min;

2: pumping in 8 ml of the blocking solution, circulating the blocking solution for 1 h and pumping out the blocking solution;

3: pumping in 8 ml of PBST, circulating PBST for 5 min, pumping out PBST and repeating to complete the step 3 times;

4: pumping in 8 ml of a diluted solution of the primary antibody, circulating the diluted solution of the primary antibody for 1 h and pumping out the diluted solution of the primary antibody;

5: pumping in 8 ml of PBST, circulating PBST for 5 min, pumping out PBST and repeating to complete the step 3 times;

6: pumping in 8 ml of a diluted solution of the secondary antibody, circulating the diluted solution of the secondary antibody for 1 h and pumping out the diluted solution of the secondary antibody;

7: pumping in 8 ml of PBST, circulating PBST for 5 min, pumping out PBST and repeating to complete the step 3 times; and 8: taking out the films and exposing the films.

A traditional method includes the following steps:

1: putting two films back-to-back into a container;

2: adding 10 ml of a blocking solution, performing vibration for 1 h and discharging the blocking solution;

3: adding 10 ml of PBST, performing vibration for 5 min and discharging PBST;

4: repeating step 3 twice;

5: adding 10 ml of a diluted solution of a primary antibody, performing vibration for 1 h and discharging the diluted solution of the primary antibody;

6: adding 10 ml of PBST, performing vibration for 5 min and discharging PBST;

7: repeating step 3 three times;

8: adding 10 ml of a diluted solution of a secondary antibody, performing vibration for 1 h and discharging the diluted solution of the secondary antibody;

9: repeating step 3 three times; and

10: taking out the films and exposing the films.

Figures 11A, 11B:
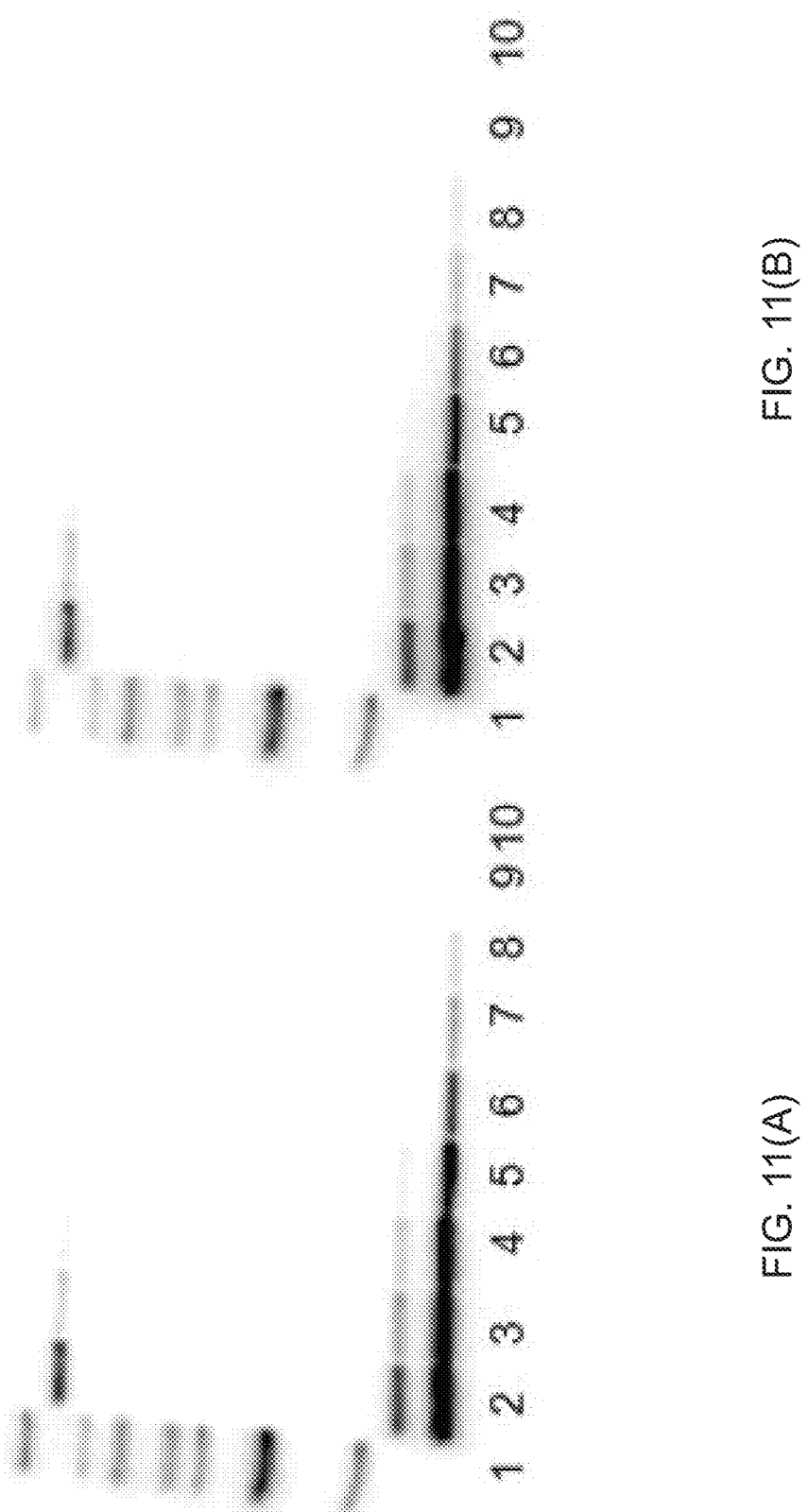
Figure 11E:
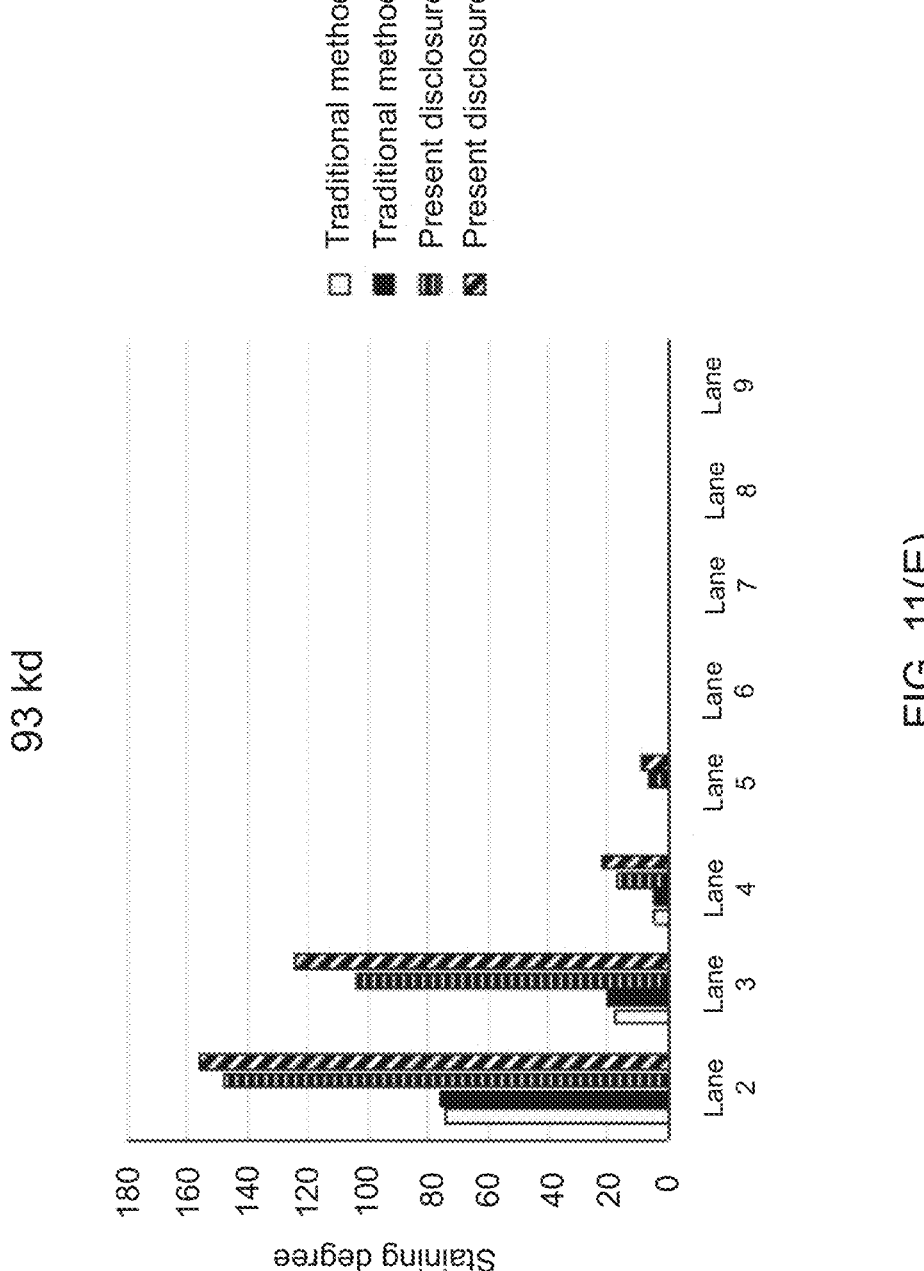
Figure 11F:
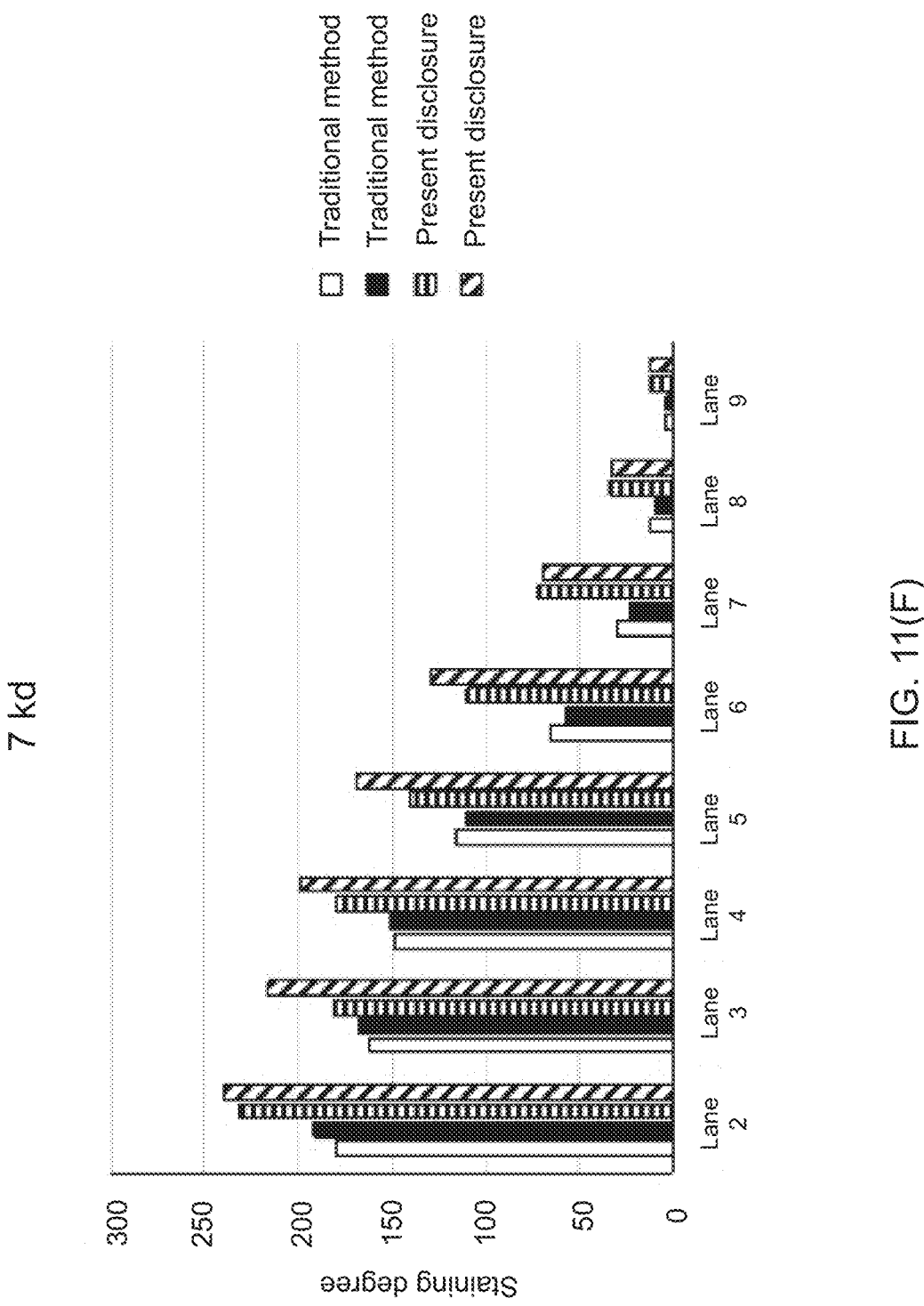

FIG. 11(A) shows results of the traditional method; FIG. 11(B) shows results of the method provided in the present disclosure; FIG. 11(C) to FIG. 11(D) show results of the method provided in the present disclosure; FIG. 11(E) shows comparative analysis of the staining degree of a 93 kd protein in the results of the traditional method and the results of the present disclosure; and FIG. 11(F) shows comparative analysis of the staining degree of a 7 kd protein in the results of the traditional method and the results of the present disclosure.

TABLE 8

| Lane | 93 kd | | 7 kd | |
| --- | --- | --- | --- | --- |
| | FIG. 11(A) | FIG. 11(B) | FIG. 11(A) | FIG. 11(B) |
| 2 | Visible | Visible | Visible | Visible |
| 3 | Visible | Visible | Visible | Visible |
| 4 | Visible | Visible | Visible | Visible |
| 5 | Invisible | Visible | Visible | Visible |
| 6 | Invisible | Invisible | Visible | Visible |
| 7 | Invisible | Invisible | Visible | Visible |
| 8 | Invisible | Invisible | Visible | Visible |
| 9 | Invisible | Invisible | Invisible | Visible |
| 10 | Invisible | Invisible | Invisible | Invisible |

TABLE 9

| 93 kd | Lane 2 | Lane 3 | Lane 4 | Lane 5 | Lane 6 | Lane 7 | Lane 8 | Lane 9 |
| --- | --- | --- | --- | --- | --- | --- | --- | --- |
| Traditional method | 74.23 | 17.51 | 4.42 | 0 | 0.00 | 0.00 | 0.00 | 0 |
| Traditional method | 76.20 | 20.04 | 5.14 | 0 | 0.00 | 0.00 | 0.00 | 0 |
| Average value | 75.21 | 18.77 | 4.78 | 0.00 | 0.00 | 0.00 | 0.00 | 0.00 |
| Present disclosure | 147.749 | 103.892 | 16.812 | 6.841 | 0 | 0 | 0 | 0 |
| Present disclosure | 156.248 | 124.363 | 22.266 | 9.112 | 0 | 0 | 0 | 0 |
| Average value | 151.9985 | 114.1275 | 19.539 | 7.9765 | 0 | 0 | 0 | 0 |
| Improvement of the present disclosure in comparison with the traditional method | 102.09% | 507.93% | 308.55% | — | — | — | — | — |

TABLE 10

| 7 kd | Lane 2 | Lane 3 | Lane 4 | Lane 5 | Lane 6 | Lane 7 | Lane 8 | Lane 9 |
| --- | --- | --- | --- | --- | --- | --- | --- | --- |
| Traditional method | 179.37 | 161.43 | 149.08 | 115.20 | 65.70 | 30.09 | 11.75 | 1.24 |
| Traditional method | 191.39 | 168.13 | 151.25 | 110.88 | 57.38 | 22.71 | 9.85 | 3.45 |
| Average value | 185.38 | 164.78 | 150.17 | 113.04 | 61.54 | 26.40 | 10.80 | 2.34 |
| Present disclosure | 232.117 | 181.525 | 180.111 | 140.909 | 109.776 | 71.938 | 33.402 | 12.461 |
| Present disclosure | 239.932 | 215.944 | 199.194 | 169.104 | 129.117 | 69.011 | 32.615 | 12.495 |
| Average value | 236.0245 | 198.7345 | 189.6525 | 155.0065 | 119.4465 | 70.4745 | 33.0085 | 12.478 |

TABLE 10-continued

| 7 kd | Lane 2 | Lane 3 | Lane 4 | Lane 5 | Lane 6 | Lane 7 | Lane 8 | Lane 9 |
|---|---|---|---|---|---|---|---|---|
| Improvement of the present disclosure in comparison with the traditional method | 27.32% | 20.61% | 26.29% | 37.13% | 94.10% | 166.95% | 205.58% | 432.91% |

It can be seen from FIGS. 11(A)-11(F) that on 93 kd, the 4th lane in the traditional method is visible, and the 5th lane in the present disclosure is visible, so that the sensitivity of the present disclosure is better.

On 7 kd, the 8th lane in the traditional method is visible, and the 9th lane in the present disclosure is visible, so that the sensitivity of the present disclosure is better.

It can be seen from FIG. 11(E), FIG. 11(F) and Tables 9-10 that compared with the traditional method, the method provided in the present disclosure has the advantages that the staining degree is increased by 102.09%-507.93% based on 93 kd detection results; and the staining degree is increased by 20.61%-432.91% based on 7 kd detection results.

In summary, compared with the traditional method, only 74% of reagents and 80% of antibodies need to be used in the present disclosure, and the sensitivity and the signal intensity of the present disclosure are better than those of the traditional method.

Example 13 WB2

On basis of the biological reaction apparatus provided in Example 4, a reaction is introduced as follows:

a 293 T cell lysis buffer is used as a sample.

The sample loading quantity is:

1: 1 ul of WB marker;
2: 20 ug of the cell lysis buffer;
3: 10 ug of the cell lysis buffer;
4: 5 ug of the cell lysis buffer;
5: 2.5 ug of the cell lysis buffer;
6: 1.25 ug of the cell lysis buffer;
7: 0.625 ug of the cell lysis buffer; and
8: 0.3125 ug of the cell lysis buffer.

A blocking solution includes 5% of skimmed milk powder and a PBS solution.

PBST is obtained by adding one thousandth of Tween 20 into PBS.

A primary antibody is rabbit anti-β-actin with a concentration of 1 mg/ml and is diluted with the blocking solution according to a ratio of 1:3000.

A secondary antibody is goat anti-rabbit HRP with a concentration of 1 mg/ml and is diluted with the blocking solution according to a ratio of 1:10000.

The present disclosure includes the following steps:

setting the temperature to be 20-30° C., the film area to be 7.5*8 CM and the flow rate to be 20 ml/min;
1: putting a film into a reactor;
2: pumping in the blocking solution;
3: pumping in PBST when the reactor is filled with the blocking solution;
4: pumping in a diluted solution of the primary antibody when the reactor is filled with PBST;
5: pumping in PBST when the reactor is filled with the diluted solution of the primary antibody;
6: pumping in a diluted solution of the secondary antibody when the reactor is filled with PBST;

7: pumping in PBST when the reactor is filled with the diluted solution of the secondary antibody;
8: continuously pumping in 2 times volume of PBST when the reactor is filled with PBST; and
9: taking out the film and performing developing.

The blocking solution, the diluted solution of the primary antibody and the diluted solution of the secondary antibody require 4 ml each, and PBST requires 16 ml.

The process of the present disclosure is completed within 2 h.

A traditional method includes the following steps:
1: putting a film into a container;
2: adding 10 ml of a blocking solution, performing vibration for 1 h and discharging the blocking solution;
3: adding 10 ml of PBST, performing vibration for 5 min and discharging PBST;
4: repeating step 3 twice;
5: adding 10 ml of a diluted solution of a primary antibody, performing vibration for 1 h and discharging the diluted solution of the primary antibody;
6: adding 10 ml of PBST, performing vibration for 5 min and discharging PBST;
7: repeating step 3 three times;
8: adding 10 ml of a diluted solution of a secondary antibody, performing vibration for 1 h and discharging the diluted solution of the secondary antibody;
9: repeating step 3 three times; and
10: taking out the film and exposing the film.

Figure 12A:
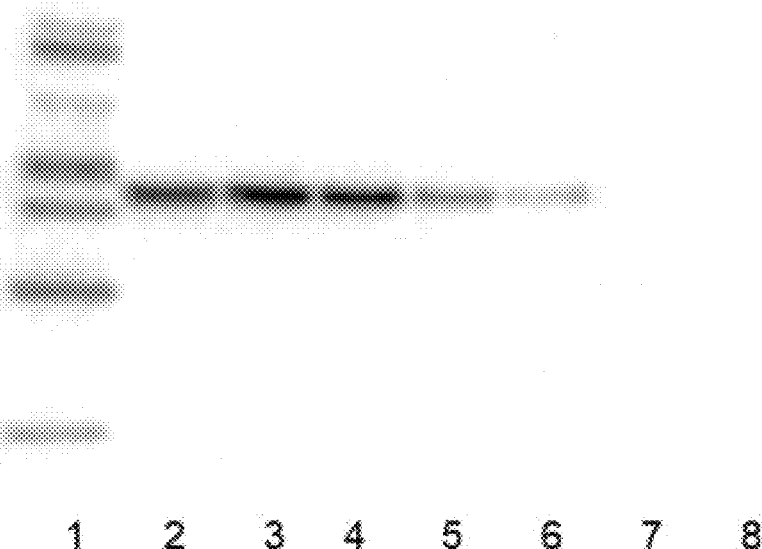
FIGS. 12(A)-12(C) show results of Example 13.
Figure 12B:
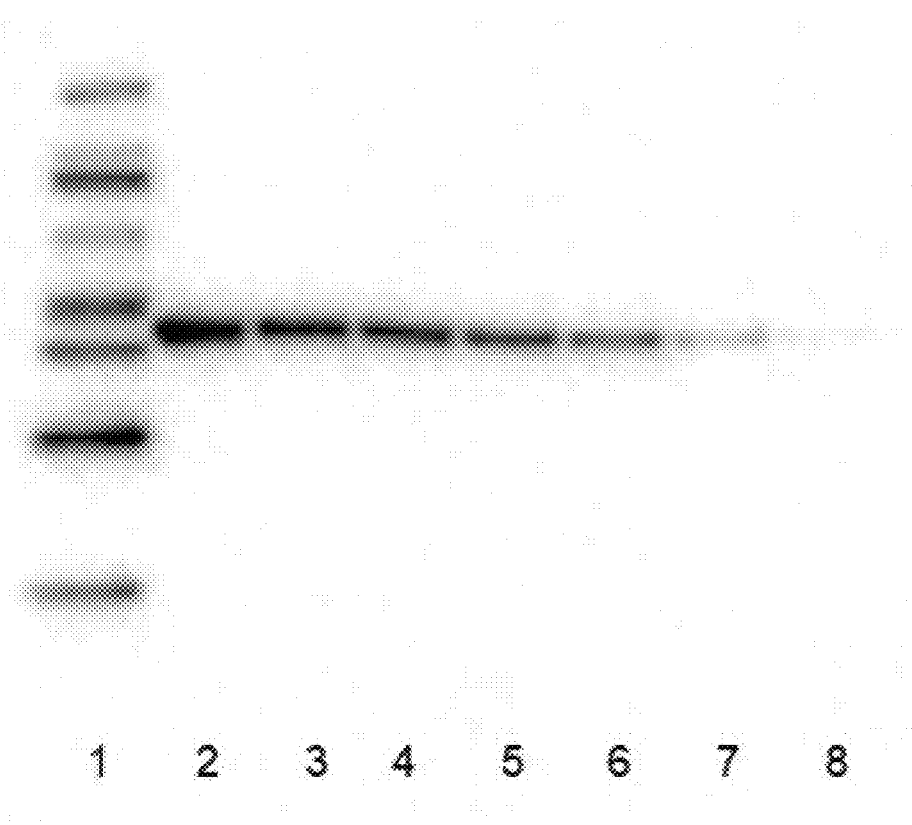
Figure 12C:
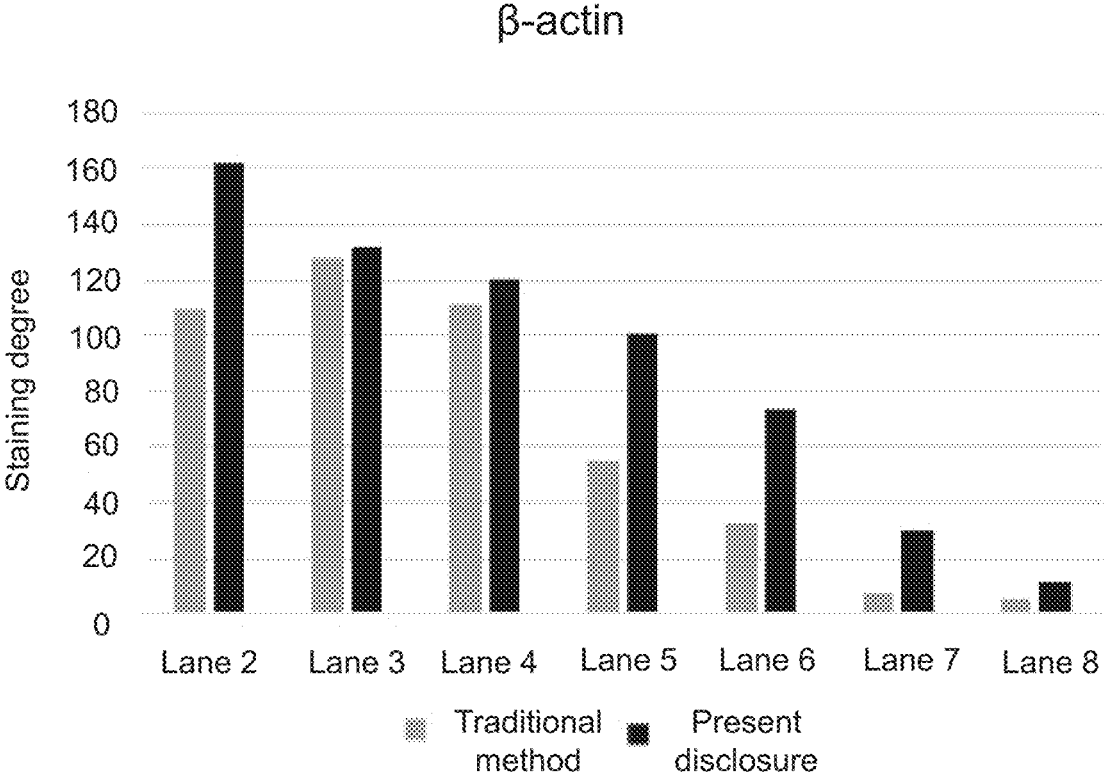

FIG. 12(A) shows results of the traditional method; FIG. 12(B) shows results of the present disclosure; and FIG. 12(C) shows comparative analysis of the staining degree of a β-actin protein in the results of the traditional method and the results of the present disclosure.

TABLE 11

| | β-actin | |
|---|---|---|
| Lane | FIG. 12(A) | FIG. 12(B) |
| 2 | Visible | Visible |
| 3 | Visible | Visible |
| 4 | Visible | Visible |
| 5 | Visible | Visible |
| 6 | Visible | Visible |
| 7 | Invisible | Visible |
| 8 | Invisible | Visible |

TABLE 12

| β-actin | Traditional method | Present disclosure | Improvement of the present disclosure in comparison with the traditional method |
|---|---|---|---|
| Lane 2 | 109.9 | 161.7 | 47.13% |
| Lane 3 | 128 | 131.9 | 3.05% |
| Lane 4 | 111.1 | 120.1 | 8.10% |
| Lane 5 | 54.7 | 100.3 | 83.36% |

TABLE 12-continued

| β-actin | Traditional method | Present disclosure | Improvement of the present disclosure in comparison with the traditional method |
|---|---|---|---|
| Lane 6 | 32.6 | 73.5 | 125.46% |
| Lane 7 | 7.5 | 30.4 | 305.33% |
| Lane 8 | 5.2 | 11.1 | 113.46% |

It can be seen from the figures that the $6^{th}$ lane in the traditional method is visible, and the $8^{th}$ lane in the present disclosure is visible, so that the sensitivity of the present disclosure is better.

It can be seen from FIG. 12(C) and Table 12 that compared with the traditional method, the method provided in the present disclosure has the advantage that the staining degree is increased by 3.05%-305.33% based on β-actin detection results.

In summary, compared with the traditional method, only 65% of reagents, 40% of antibodies and a shorter processing time need to be used in the present disclosure, and the sensitivity and the signal intensity of the present disclosure are better than those of the traditional method.

Example 14 WB5

On basis of the biological reaction apparatus provided in Example 3, a reaction is introduced as follows:

a 293 T cell lysis buffer is used as a sample.

The sample loading quantity is:

1: 1 ul of WB marker;

2: 20 ug of the cell lysis buffer;

3: 10 ug of the cell lysis buffer;

4: 5 ug of the cell lysis buffer;

5: 2.5 ug of the cell lysis buffer; and

6: 1.25 ug of the cell lysis buffer.

A primary antibody is mouse anti-GAPDH.

A secondary antibody is goat anti-mouse.

The present disclosure includes the following steps:

1: putting a film B into a reactor 14-1 and a film D into a reactor 14-2;

2: connecting the reactor 14-1 and the reactor 14-2 in series and setting the temperature to be 20-30° C., the area of the film B and the film D to be 7.5*4 CM and the flow rate to be 10 ml/min;

3: pumping in a blocking solution, circulating the blocking solution for 1 h after the reactor 14-1 and the reactor 14-2 are filled with the blocking solution and pumping out the blocking solution;

4: pumping in PBST, circulating PBST for 5 min, pumping out PBST and repeating to complete the step 3 times;

5: pumping in a diluted solution of the primary antibody, circulating the diluted solution of the primary antibody for 1 h and pumping out the diluted solution of the primary antibody;

6: pumping in PBST, circulating PBST for 5 min, pumping out PBST and repeating to complete the step 3 times;

7: pumping in a diluted solution of the secondary antibody, circulating the diluted solution of the secondary antibody for 1 h and pumping out the diluted solution of the secondary antibody;

8: pumping in PBST, circulating PBST for 5 min, pumping out PBST and repeating to complete the step 3 times; and 9: taking out the films and exposing the films.

The blocking solution, the diluted solution of the primary antibody and the diluted solution of the secondary antibody require 8 ml each, and PBST requires 7 ml.

A traditional method includes the following steps:

1: putting two films (A and C) into containers respectively;

2: separately adding 10 ml of a blocking solution, performing vibration for 1 h and discharging the blocking solution;

3: separately adding 10 ml of PBST, performing vibration for 5 min and discharging PBST;

4: repeating step 3 twice;

5: separately adding 10 ml of a diluted solution of a primary antibody, performing vibration for 1 h and discharging the diluted solution of the primary antibody;

6: separately adding 10 ml of PBST, performing vibration for 5 min and discharging PBST;

7: repeating step 3 three times;

8: separately adding 10 ml of a diluted solution of a secondary antibody, performing vibration for 1 h and discharging the diluted solution of the secondary antibody;

9: repeating step 3 three times; and

10: taking out the films and exposing the films.

Figure 13D:
Figure 13D:
Figure 13C:
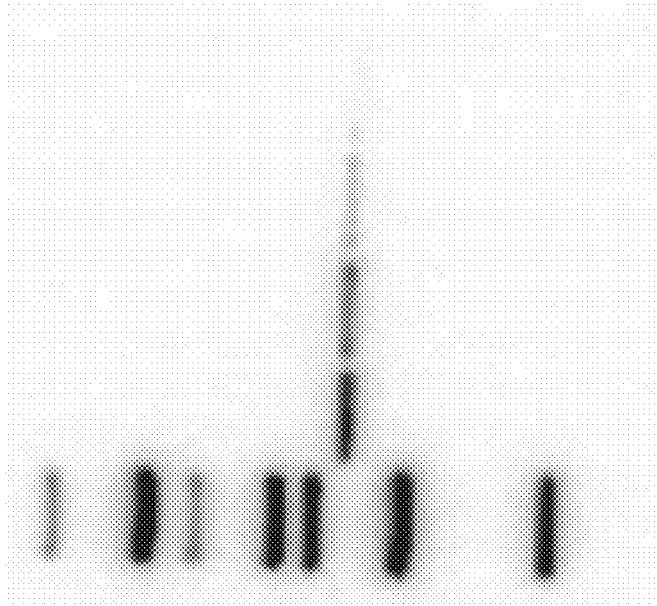

FIG. 13(A) shows results of the film A; FIG. 13(B) shows results of the film B; FIG. 13(C) shows results of the film C; FIG. 13(D) shows results of the film D; and FIG. 13(E) shows comparative analysis of the staining degree of a GAPDH protein in the results of the traditional method and the results of the present disclosure.

TABLE 13

| GAPDH | Lane 2 | Lane 3 | Lane 4 | Lane 5 |
|---|---|---|---|---|
| Film A | 79.7 | 60.3 | 29.9 | 9.4 |
| Film B | 154.3 | 124.4 | 43.1 | 12.3 |
| Film C | 84.5 | 54 | 20.6 | 3.9 |
| Film D | 143.6 | 114.3 | 44.6 | 7.7 |
| Average value of the film A and the film C | 82.1 | 57.15 | 25.25 | 6.65 |
| Average value of the film B and the film D | 148.95 | 119.35 | 43.85 | 10 |
| Improvement of the present disclosure in comparison with the traditional method | 81.43% | 108.84% | 73.66% | 50.38% |

Figure 13E:
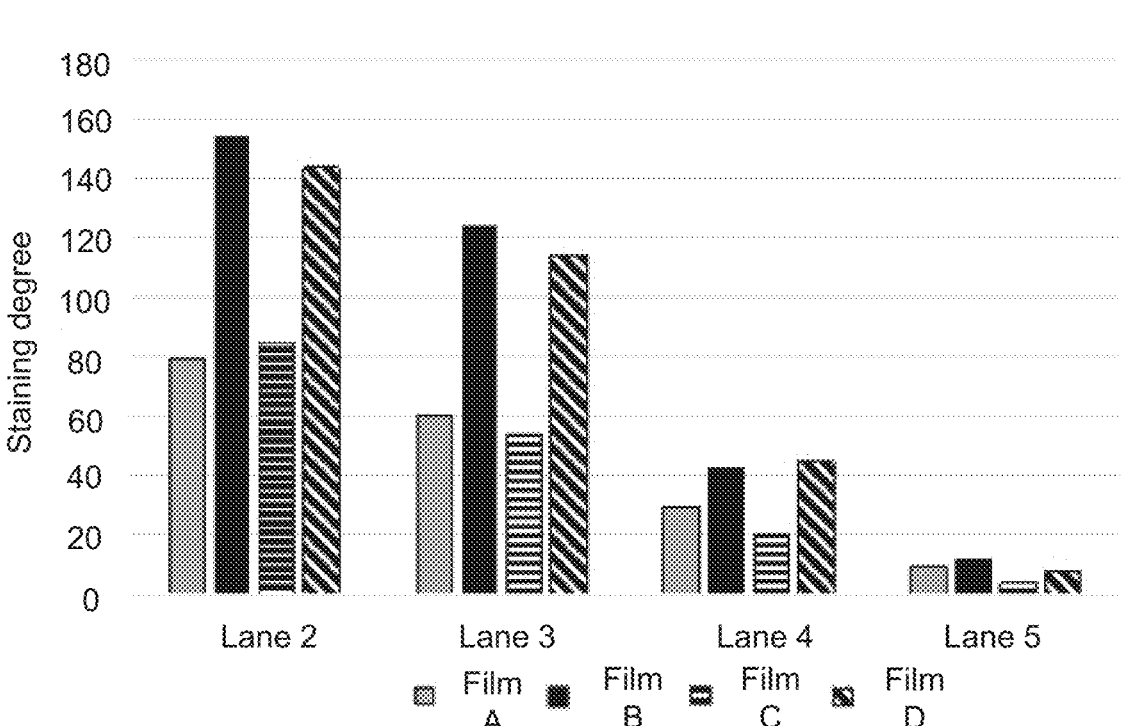

It can be seen from the figures that the color of FIG. 13(B) and FIG. 13(D) is darker than that of FIG. 13(A) and FIG. 13(C), and it can be seen from FIG. 13(E) and Table 13 that compared with the traditional method, the method provided in the present disclosure has the advantage that the staining degree is increased by 50.38%-108.84% based on GAPDH detection results. That is to say, the signal intensity is higher, and it is further shown that the effect of the present disclosure is better than that of the traditional method. In summary, compared with the traditional method, only 66% of reagents need to be used in the present disclosure, and the sensitivity and the signal intensity of the present disclosure are better than those of the traditional method.

Example 15 WB3

On basis of the biological reaction apparatus provided in Example 5, a reaction is introduced as follows:

a 293 T cell lysis buffer is used as a sample.

The sample loading quantity is:

1: 20 ug of the cell lysis buffer;

2: 10 ug of the cell lysis buffer;

3: 5 ug of the cell lysis buffer;

4: 2.5 ug of the cell lysis buffer;

5: 1.25 ug of the cell lysis buffer; and

6: 0.625 ug of the cell lysis buffer.

A blocking solution includes 5% of skimmed milk powder and a PBS solution.

PBST is obtained by adding one thousandth of Tween 20 into PBS.

A primary antibody is rabbit anti-β-actin with a concentration of 1 mg/ml and is diluted with the blocking solution according to a ratio of 1:3000.

A secondary antibody is goat anti-rabbit HRP with a concentration of 1 mg/ml and is diluted with the blocking solution according to a ratio of 1:10000.

The present disclosure includes the following steps:

1: setting the temperature to be 20-30° C., the film area to be 7.5*4 CM and the flow rate to be 10 ml/min;

2: pumping in 5 ml of the blocking solution, circulating the blocking solution for 1 h and pumping out the blocking solution;

3: pumping in 5 ml of PBST, circulating PBST for 5 min, pumping out PBST and repeating to complete the step 3 times;

4: pumping in 5 ml of a mixed solution of the primary antibody and the secondary antibody, circulating the mixed solution for 1 h and pumping out the mixed solution for recovery;

5: pumping in 5 ml of PBST, circulating PBST for 5 min, pumping out PBST and repeating to complete the step 3 times;

6: pumping in a developing solution and pumping out the developing solution after a reactor is filled with the developing solution; and 7: taking out a film and performing developing.

A traditional method includes the following steps:

1: putting a film back-to-back into a container;

2: adding 10 ml of a blocking solution, performing vibration for 1 h and discharging the blocking solution;

3: adding 10 ml of PBST, performing vibration for 5 min and discharging PBST;

4: repeating step 3 twice;

5: adding 10 ml of a diluted solution of a primary antibody, performing vibration for 1 h and discharging the diluted solution of the primary antibody;

6: adding 10 ml of PBST, performing vibration for 5 min and discharging PBST;

7: repeating step 3 three times;

8: adding 10 ml of a diluted solution of a secondary antibody, performing vibration for 1 h and discharging the diluted solution of the secondary antibody;

9: repeating step 3 three times; and

10: taking out the film and exposing the film.

Figure 14B:
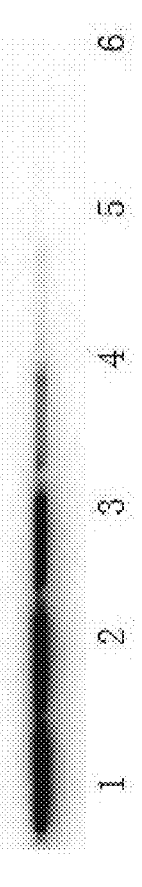
FIGS. 14(A)-14(C) show results of Example 14.
Figure 14A:
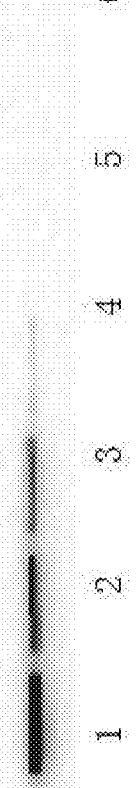
Figure 14C:
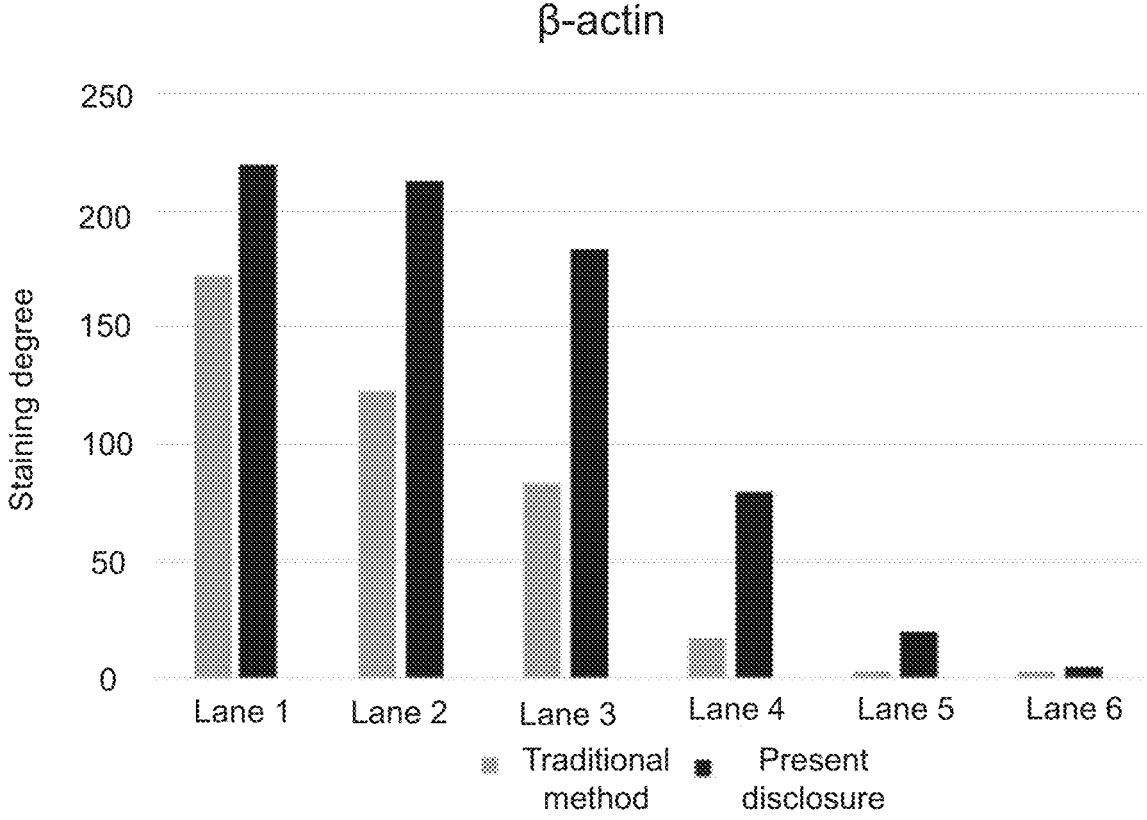

FIG. 14(A) shows results of the traditional method; FIG. 14(B) shows results of the present disclosure; and FIG. 14(C) shows comparative analysis of the staining degree of a β-actin protein in the results of the traditional method and the results of the present disclosure.

TABLE 14

| | β-actin | |
| Lane | FIG. 14(A) | FIG. 14(B) |
| --- | --- | --- |
| 1 | Visible | Visible |
| 2 | Visible | Visible |
| 3 | Visible | Visible |
| 4 | Visible | Visible |
| 5 | Invisible | Visible |
| 6 | Invisible | Invisible |

TABLE15

| β-actin | Traditional method | Present disclosure | Improvement of the present disclosure in comparison with the traditional method |
| --- | --- | --- | --- |
| Lane 1 | 171.9 | 219.2 | 27.52% |
| Lane 2 | 122.8 | 212 | 72.64% |
| Lane 3 | 82.7 | 183.2 | 121.52% |
| Lane 4 | 16.7 | 79.7 | 377.25% |
| Lane 5 | 2.8 | 19.7 | 603.57% |
| Lane 6 | 2.9 | 4.7 | 62.07% |

It can be seen from FIGS. 14(A)-14(C) that the $4^{th}$ lane in the traditional method is visible, and the $5^{th}$ lane in the present disclosure is visible, so that the sensitivity of the present disclosure is better.

It can be seen from FIG. 14(C) and Table 15 that compared with the traditional method, the method provided in the present disclosure has the advantage that the staining degree is increased by 27.52%-603.57% based on β-actin detection results.

In summary, compared with the traditional method, only 30% of reagents and a shorter processing time need to be used in the present disclosure, and the sensitivity and the signal intensity of the present disclosure are better than those of the traditional method.

Example 16 WB4

On basis of the biological reaction apparatus provided in Example 6, a reaction is introduced as follows:

a protein with an His tag and the molecular weight of 7 kd is used as a sample.

The sample loading quantity is:

1:10 ng of His protein;

2: 5 ng of His protein;

3: 2.5 ng of His protein;

4: 1.25 ng of His protein;

5: 0.6 ng of His protein; and

6: 0.3 ng of His protein.

A blocking solution includes 5% of skimmed milk powder and a PBS solution. PBST is obtained by adding one thousandth of Tween 20 into PBS.

A primary antibody is mouse anti-His with a concentration of 1 mg/ml and is diluted with the blocking solution according to a ratio of 1:3000.

A secondary antibody is goat anti-mouse HRP with a concentration of 1 mg/ml and is diluted with the blocking solution according to a ratio of 1:10000.

Figure 15B:
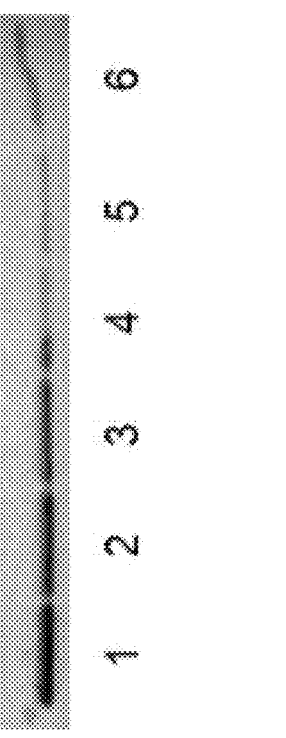
Figure 15A:
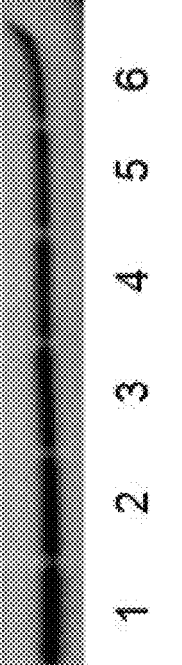
Figure 15C:
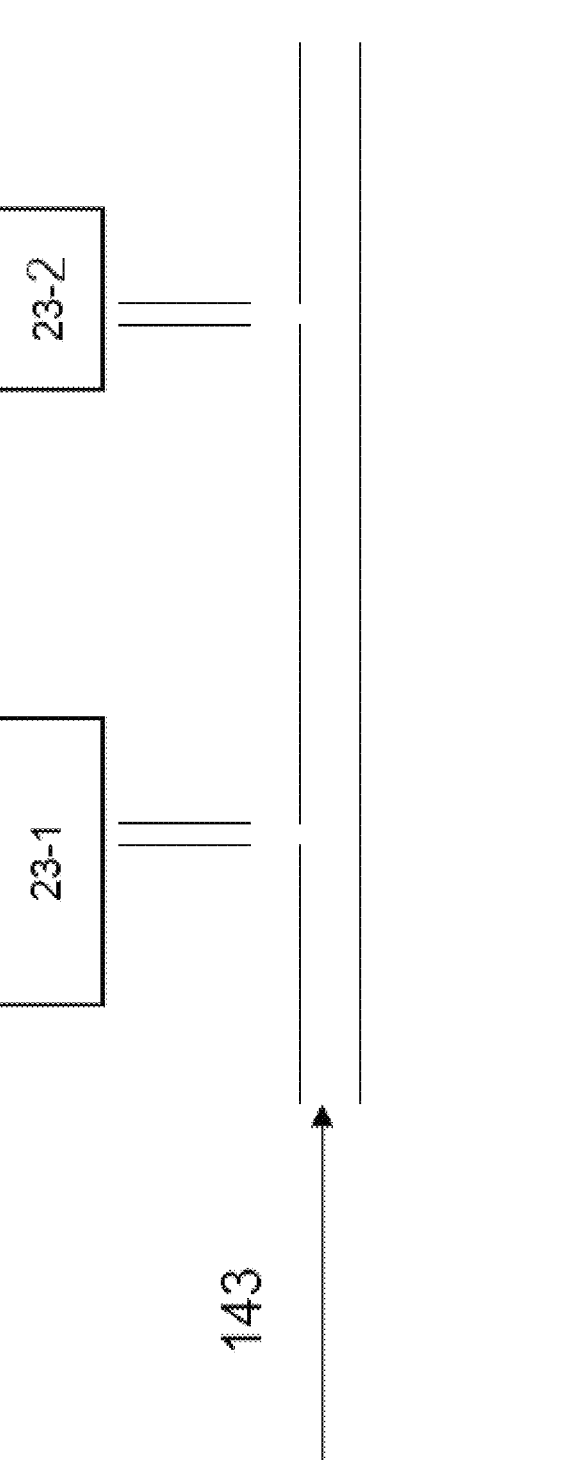

The present disclosure includes the following steps:

1: setting the temperature to be 20-30° C., the film area to be 7.5*8 CM and the flow rate to be 20 ml/min;

2: adding a primary antibody mother liquid and a secondary antibody mother liquid into corresponding reservoirs (as shown in FIG. 15(C), 23-1 refers to a secondary antibody mother liquid pool, 23-2 refers to a primary antibody mother liquid pool, and 143 refers to a liquid flow direction);

3: pumping in 5 ml of the blocking solution, where antibodies are diluted and introduced into a reactor when the blocking solution flows through the reservoirs; and circulating the blocking solution for 1 h and pumping out the blocking solution;

4: pumping in 5 ml of PBST, circulating PBST for 5 min, pumping out PBST and repeating to complete the step 3 times;

5: pumping in a TMB color developing solution and pumping out the TMB color developing solution; and 6: observing conditions from an observation window and recording results.

A traditional method includes the following steps:

1: putting a film back-to-back into a container;

2: adding 10 ml of a blocking solution, performing vibration for 1 h and discharging the blocking solution;

3: adding 10 ml of PBST, performing vibration for 5 min and discharging PBST;

4: repeating step 3 twice;

5: adding 10 ml of a diluted solution of a primary antibody, performing vibration for 1 h and discharging the diluted solution of the primary antibody;

6: adding 10 ml of PBST, performing vibration for 5 min and discharging PBST;

7: repeating step 3 three times;

8: adding 10 ml of a diluted solution of a secondary antibody, performing vibration for 1 h and discharging the diluted solution of the secondary antibody;

9: repeating step 3 three times; and

10: adding a TMB color developing solution into the container and recording results.

FIG. 15(B) shows results of the traditional method; FIG. 15(A) shows results of the present disclosure; FIG. 15(C) shows the liquid flow direction of the primary antibody mother liquid and the secondary antibody mother liquid added into corresponding reservoirs; and FIG. 15(D) shows comparative analysis of the staining degree of a 7 kd protein in the results of the traditional method and the results of the present disclosure.

TABLE 16

| 7 kd | Traditional method | Present disclosure | Improvement of the present disclosure in comparison with the traditional method |
|---|---|---|---|
| Lane 1 | 48.4 | 97.2 | 100.83% |
| Lane 2 | 55.5 | 115.4 | 107.93% |
| Lane 3 | 67.3 | 134.2 | 99.41% |
| Lane 4 | 77.3 | 163.2 | 111.13% |
| Lane 5 | 84.5 | 174 | 105.92% |
| Lane 6 | 96.7 | 154 | 59.26% |

Figure 15D:
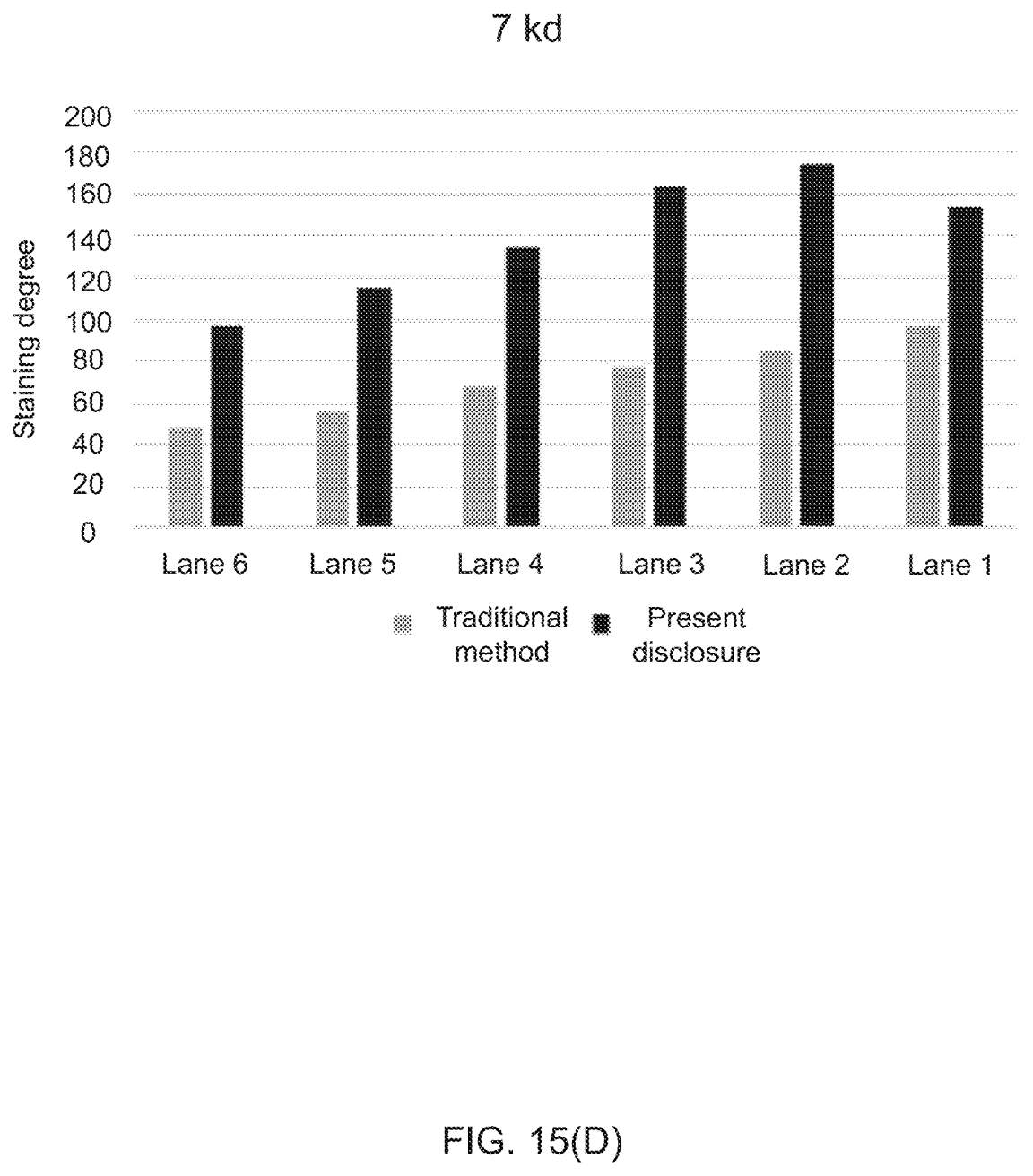

It can be seen from FIG. 15(D) and Table 16 that bands in the present disclosure are darker than those in the traditional method, and the staining degree is increased by 59.26%-111.13%, showing that the effect of the present disclosure is better.

In summary, compared with the traditional method, only 20% of reagents and a shorter processing time need to be used in the present disclosure, and the signal intensity of the present disclosure is better than that of the traditional method.

Descriptions above are only preferred embodiments of the present disclosure. It should be pointed out that many improvements and modifications may be made by those of ordinary skill in the art without departing from the principle of the present disclosure, and those improvements and modifications also fall within the protection scope of the present disclosure.

What is claimed is:

1. A biological reaction apparatus, comprising a power supply module, a control module, a liquid processing module, a reactor module and a sensor; wherein the power supply module comprises a direct current power supply and a switch;

the control module comprises a system controller, an input device and an output device;

the liquid processing module comprises a valve or a combination of valves, a pump or a combination of pumps and sample cells;

the reactor module comprises a reactor;

the power supply module is separately connected to the control module, the liquid processing module and the reactor module through cables;

the control module is separately connected to the liquid processing module and the reactor module through the cables;

the liquid processing module is connected to the reactor module through a pipeline and configured to input a reactant to the reactor; and the control module is connected to the reactor module through the sensor, wherein the reactor comprises a reactor frame, a pressing part, a sealing part, and a rotating shaft, the reactor frame includes a reactor front plate, a reactor rear plate, and a limiting part, and a reactor cavity is formed between the reactor front plate and the reactor rear plate, the limiting part is arranged in the reactor cavity between the reactor front plate and the reactor rear plate and configured to maintain the reactor cavity after the reactor is closed, the pressing part is configured to press the reactor front plate and the reactor rear plate after the reactor is closed, and the pressing part is fixed to the reactor frame through the rotating shaft and is rotatable around the rotating shaft, the sealing part is arranged between the reactor front plate and the reactor rear plate to seal the reactor cavity, at least one opening is formed on the reactor frame, and a liquid flow or a gas flow enters the reactor cavity through the at least one opening and flows through a gap between the reactant and the reactor cavity to make the reactant suspended in the reactor cavity; and the biological reaction apparatus further comprises a waste liquid collector configured to receive waste liquid from the reactor, a liquid level indicator, an air inlet pipeline, and a gas-liquid selection valve, wherein:

the liquid level indicator is maintained below a liquid level of the waste liquid collector, the air inlet pipeline is maintained above the liquid level of the waste liquid collector to ensure that waste liquid is not sucked into the pipeline when the gas flow is introduced, and the gas-liquid selection valve is connected to a tail end of the air inlet pipeline to ensure that gas intake and liquid discharge are isolated.

2. The biological reaction apparatus according to claim 1, wherein a mother liquid pool is also arranged between the liquid processing module and the reactor module.

3. The biological reaction apparatus according to claim 1, wherein an inner wall of the reactor is subjected to hydrophobization treatment or hydrophilization treatment; wherein the hydrophobization treatment is one or more of siliconization and alkylation; and wherein the hydrophilization treatment is one or more of hydroxylation, carboxylation and amination.

4. The biological reaction apparatus according to claim 1, wherein the reactor is made from a metal material or a polymer material, the metal material is selected from stainless steel and aluminum alloy, and the polymer material is selected from polypropylene and an acrylonitrile-styrene-butadiene copolymer.

5. The biological reaction apparatus according to claim 1, wherein the sealing part is made from an elastic material or a material repellent to a reaction solution in the biological reaction apparatus.

6. The biological reaction apparatus according to claim 1, wherein the reactor module further comprises an identification module, wherein the identification module is RFID.

7. The biological reaction apparatus according to claim 1, wherein the liquid processing module comprises one or more sample storage containers, and the sample storage containers are the sample cells.

8. The biological reaction apparatus according to claim 1, wherein the liquid processing module comprises at least one one-way and/or two-way pump, wherein the pump is one or more of a peristaltic pump, a diaphragm pump, a gear pump and a plunger pump.

9. The biological reaction apparatus according to claim 1, wherein the valve is one or more of a diaphragm valve, a pinch valve and a column valve.

10. The biological reaction apparatus according to claim 1, wherein the reactor is connected to the liquid processing module through the pipeline, a one-way valve or a two-way fast connector.

11. The biological reaction apparatus according to claim 1, wherein a liquid film or a gas film is formed between the reactant and a wall of the reactor to prevent a wall attachment effect of the reactant.

12. The biological reaction apparatus according to claim 1, wherein the at least one opening includes two liquid inlets arranged on the reactor front plate and the reactor rear plate, respectively.

13. The biological reaction apparatus according to claim 1, wherein the pressing part includes a front pressing structure arranged on the reactor front plate and a rear pressing structure arranged on the reactor rear plate, each of the front pressing structure and the rear pressing structure is fixed through the rotating shaft and is rotatable around the rotating shaft.

14. The biological reaction apparatus according to claim 1, further comprising at least one diversion block arranged within the reactor cavity to make the liquid flow entering the reactor cavity uniformly distributed.

15. The biological reaction apparatus according to claim 1, further comprising a two-way fast card set configured to connect the pipeline and the reactor, the two-way fast card set including a first fast card and a second fast card, wherein:

the first fast card comprises a first pagoda connector, a closure member, a first main body, a conductor, a first guide structure, an inner limiting structure, an outer limiting structure, and a first one-way valve function, the first pagoda connector is connected to one of the pipeline or the reactor, and includes a first internal flow channel, the closure member and the first main body form a containing cavity, the conductor includes a second internal flow channel, the inner limiting structure limits a backward distance of the conductor, and the outer limiting structure limits an outward distance of the conductor, the second fast card comprises a second main body, a second pagoda connector, a second guide structure, and a second one-way valve structure, the second pagoda connector is connected to the other one of the reactor and the pipeline, and includes a third internal flow channel, the first guide structure and the second guide structure are configured for internal guide fixation, the first one-way valve function and the second one-way valve structure are configured to control the first fast card to separate from the second fast card, when the first fast card and the second fast card are connected, the third internal flow channel, the second internal flow channel, and the first internal flow channel are in communication.

* * * * *